United States Patent [19] [11] 4,139,560
Reinehr et al. [45] Feb. 13, 1979

[54] NONYLAMINES

[75] Inventors: Dieter Reinehr, Wittlingen, Fed. Rep. of Germany; Bernard Hugelin, Gaillard, France; Eduard Troxler, Basel, Switzerland

[73] Assignee: Ciba Geigy Corporation, Ardsley, N.Y.

[21] Appl. No.: 775,654

[22] Filed: Mar. 3, 1977

Related U.S. Application Data

[62] Division of Ser. No. 551,481, Feb. 20, 1975, abandoned.

[30] Foreign Application Priority Data

Feb. 22, 1974 [CH] Switzerland ............................ 2544/74
Sep. 13, 1974 [CH] Switzerland .......................... 12518/74

[51] Int. Cl.² ............................................. C07C 87/28
[52] U.S. Cl. ......................... 260/570.8 R; 260/326.15; 260/329 AM; 260/347.7; 260/563 R; 260/583 H; 260/566 F; 424/330; 546/329; 546/139; 546/176
[58] Field of Search ...................... 260/570.8 R, 347.7, 260/576, 578, 571

[56] References Cited

U.S. PATENT DOCUMENTS 2,276,587  3/1942  Mettler et al. ................ 260/570.8 X Primary Examiner—Robert V. Hines
Attorney, Agent, or Firm—Wenderoth, Lind & Ponack

[57] ABSTRACT

New nonadienylamines, nonatrienylamines and nonylamines are described, as well as a new process for their manufacture by reacting a 1,3-diolefine with a Schiff's base in the presence of certain nickel catalysts. The new compounds are suitable for combating micro-organisms, for example in the protection of materials.

4 Claims, No Drawings

NONYLAMINES

This is a division of application Ser. No. 551,481 filed on Feb. 20, 1975 now abandoned.

The present invention relates to new nonylamines, a new process for their manufacture and the use of the new compounds for combating micro-organisms, especially for the protection of materials.

It has been found that compounds of the formula Ia and/or Ib

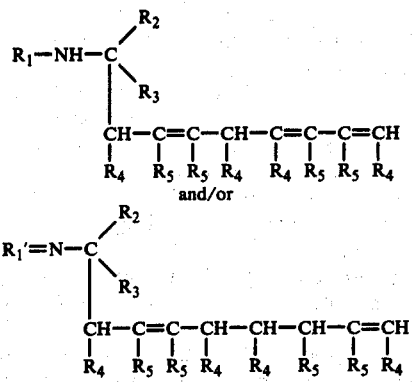

and the corresponding hydrogenated derivatives of the formula Ic

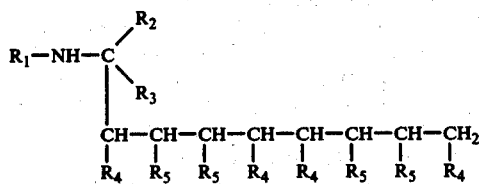

wherein $R_1$ represents an alkyl, cycloalkyl or aralkyl group, $R_1'$ represents an alkylidene, cycloalkylidene or aralkylidene group corresponding to $R_1$, $R_2$ represents hydrogen or an alkyl group and $R_3$ represents hydrogen, an alkyl or aralkyl group, a 1-nuclear to 4-nuclear carbocyclic-aromatic group or a 1-nuclear to 3-nuclear heterocyclic-aromatic group which is linked to the C atom otherwise than in the α-position to a nitrogen atom, or $R_2$ and $R_3$ conjointly form a 4-membered to 11-membered alkylene or oxaalkylene chain, and groups according to the definition which are represented by $R_1$, $R_1'$, $R_2$ and $R_3$ can be substituted, but are free from proton-active groups, azide groups and/or groups containing multiple bonds, and $R_4$ and $R_5$ independently of one another represent hydrogen or an alkyl group having 1–4 carbon atoms which contains at least one hydrogen atom on the linking C atom, the C number of the substituents $R_4$ and $R_5$ on four successive chain members being not more than 5, can be prepared by reacting a 1,3-diolefine of the formula II

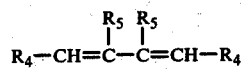

in which what is specified under the formulae Ia – Ic applies to $R_4$ and $R_5$, at a temperature of $-50°$ C to $+100°$ C, in the presence of a catalyst which, with the optional addition of an electron-donor, is obtained by reducing a nickel compound which is free from carbon monoxide, and optionally in the presence of a basic accelerator of the reaction, with a compound of the formula III

in which what is specified under the formulae Ia – Ic applies to $R_1$, $R_2$ and $R_3$, and, optionally, by hydrogenating the resulting reaction product of the formula Ia or Ib.

It is known from the literature that the catalytic reaction of 1,3-diolefines with azines gives cyclic compounds, namely 1,2-diazacyclododecatrienes-1,5,9, under analogous reaction conditions. Furthermore, it is known to use certain Schiff's bases, such as 1-(2'-pyridylmethyleneamino)-2-(N,N-dimethylamino)-ethane, as a ligand in nickel complex catalysts for the co-oligomerisation of butadiene and ethylene. In this co-oligomerisation, trans-1,4,9-decatriene is formed as the main product, with smaller proportions of 1,3,9-decatriene and 2,4,9-decatriene and/or cyclododecatriene.

In view of this state of the art, it is surprising, on the one hand, that the Schiff's bases of the formula III can be made to react catalytically in the process according to the invention. On the other hand, it was not to be expected that the co-oligomerisation of a 1,3-diolefine with a compound of the formula III would give open-chain products exclusively, and, in fact, the co-oligomerisation products of 2 mols of 1,3-diolefine of the formula II and 1 mol of Schiff's base of the formula III are formed with a high degree of selectivity, even if the 1,3-diolefine of the formula II is employed in excess. In addition, it is possible, by adding reaction accelerators, to achieve a high velocity in the homogeneous nickel-(O)-ligand catalysis according to the invention.

Groups according to the definition, which are represented by $R_1$, $R_1'$, $R_2$ and $R_3$, can be unsubstituted or substituted, but should be free from proton-active groups, azide groups and/or groups containing multiple bonds, such as —OH, —COOH, —SH, —CHO, —NO$_2$ or —CN groups or alkenyl or alkinyl radicals. Examples of possible substituents are halogen atoms, such as fluorine, chlorine or bromine, trifluoromethyl and phenyl groups, or alkyl, alkoxy, n-monoalkylamino, N,N-dialkylamino or alkylthio groups, each having 1 – 4 carbon atoms in the alkyl or alkoxy part.

Possible alkyl or alkylidene groups within the meaning of $R_1$, $R_1'$, $R_2$ and $R_3$, are above all straight-chain or branched groups having 1-18, preferably 1-8, carbon atoms. If such groups are substituted, for example by halogen atoms or alkoxy, N-monoalkylamino or N,N-dialkylamino groups having 1-4 carbon atoms in the alkyl or alkoxy part, these substituents are preferably not in the α-position to the N or C atom to which the groups $R_1$, $R_1'$, $R_2$ or $R_3$ are linked. The following examples of such alkyl groups may be mentioned: the methyl, ethyl, 2-ethoxyethyl, n-propyl, isopropyl, 2-methylpropyl, 2,2-dimethylpropyl, 2-bromo-2-methylpropyl, 3-N-methylaminopropyl, 3-N,N-di-n-butylaminopropyl, n-butyl, sec.-butyl, tert.-butyl, 2-methylbutyl, 3-methylbutyl, 3,3-dimethylbutyl, 2-bromo and 2-chlorobutyl, 2-chloro-2,3-dimethylbutyl, 2,3-dibromobutyl, 2-N,N-diethylaminobutyl, 3-methoxybutyl, n-pentyl, 4-methyl-pentyl, n-hexyl, 3- bromohexyl, 3-chloro-2,3-dimethylhexyl, 3-ethylhexyl, n-heptyl, 2-N-methylaminoheptyl, 5-chloro-2,5-N,N-dimethylaminoheptyl, n-octyl, n-decyl, n-dodecyl, n-tetradecyl and n-octadecyl groups, as well as the corresponding alkylidene groups.

If $R_1$ and $R_1'$ respectively represent a cycloalkyl or cycloalkylidene group, this preferably has 4–12, especially 5–8, carbon atoms and can be substituted, for example by halogen atoms, such as fluorine, chlorine or bromine, or alkyl or alkoxy groups having 1–4, especially 1 or 2, carbon atoms. The following examples may be mentioned: cyclobutyl, cyclopentyl, 2-propyl-cyclopentyl, cyclohexyl, fluoro-, chloro-, bromo- or methyl-cyclohexyl, N,N-diethylaminocyclohexyl, methylcycloheptyl, cyclooctyl and cyclododecyl groups, as well as the corresponding cycloalkylidene groups.

Aralkyl or aralkylidene groups which are represented by $R_1$, $R_1'$ or $R_3$, preferably have 7–11 carbon atoms and can be substituted, for example by halogen atoms or alkyl or alkoxy groups having 1–4, especially 1 or 2, carbon atoms. Examples of such groups are: the benzyl, β-phenylethyl,α-methylnaphthyl, 4-bromobenzyl, 3-fluorobenzyl, 4-methoxybenzyl and 4-methylbenzyl groups, as well as the corresponding aralkylidene groups.

If $R_3$ represents a 1-nuclear to 4-nuclear carbocyclicaromatic group, it is, for example, the phenyl, naphthyl, phenanthryl, anthryl, fluoranthenyl, pyrenyl, triphenylenyl and naphthacenyl groups, which can be substituted, for example, by halogen atoms, especially chlorine, or trifluoromethyl, alkyl, alkoxy, N-monoalkylamino or N,N-dialkylamino groups, each having 1–4 carbon atoms in the alkyl or alkoxy part. Naphthyl groups, and particularly phenyl groups, are preferred.

Possible 1-nuclear to 3-nuclear heterocyclic-aromatic groups $R_3$ are ring systems containing S, O and/or N, above all 5-membered and 6-membered ring systems, such as, for example, furyl-2, furyl-3, thienyl-3, thienyl-2, oxazolyl-4 or oxazolyl-5, isoxazolyl-4 or isoxazolyl-5, indolyl-3, pyrrolyl-3, pyrazolyl-4, pyridazolyl-4 or pyridazolyl-5, isothiazolyl-4, pyrimidinyl-5, pyridyl-3 or pyridyl-4, quinolyl-3 or quinolyl-4, isoquinolyl-4, cinnolinyl-4, naphthyridyl-3 or naphthyridyl-4, benzo[b]thienyl-3, naphtho[2,3-b]thienyl-2 or naphtho [2,3-b]thienyl-3, isobenzofuranyl-1, carbazolyl-2, phenanthridinyl-3, acridinyl-2, 1,7-phenanthrolinyl-3, phenazinyl-1 and phenothiazinyl-2 groups which can be substituted, for example, by halogen atoms or alkyl or alkoxy groups having 1–4, especially 1 or 2, carbon atoms. The furyl, thienyl, pyridyl-3 and pyridyl-4 groups are particularly preferred.

Possible substituents on alkylene or oxaalkylene chains formed by $R_2$ conjointly with $R_3$, are above all halogen atoms or alkyl and alkoxy groups having 1–4, especially 1 or 2, carbon atoms. Thus, $R_2$ and $R_3$, conjointly with the carbon atom to which they are linked, form, for example, a cyclopentyl, cyclohexyl, methylcyclohexyl, chlorocyclohexyl, tetrahydrofuryl, 3-methyltetrahydrofuryl, tetrahydropyranyl, cycloheptyl, cyclooctyl, cyclodecyl or cyclododecyl group.

Preferred compounds are those of the formulae Ia – Ic, wherein $R_1$ and $R_2$ respectively represent an unsubstituted alkyl or alkylidene group having 1–18 carbon atoms, an unsubstituted cycloalkyl or cycloalkylidene group having 5–8 carbon atoms, a benzyl or β-phenylethyl group or a benzylidene or β-phenylethylidene group, $R_2$ represents hydrogen or an unsubstituted alkyl group having 1 – 18 carbon atoms, and $R_3$ represents hydrogen, an unsubstituted alkyl group having 1 – 18 carbon atoms, a benzyl or β-phenethyl group, a phenyl group which is unsubstituted or is substituted by halogen atoms or alkyl or alkoxy groups having 1 – 4 carbon atoms, a naphthyl-1 or naphthyl-2 group or an unsubstituted, mononuclear heterocyclic-aromatic group which is linked to the C atom otherwise than in the α-position to a nitrogen atom, or $R_2$ and $R_3$ conjointly form an unsubstituted, 4-membered to 11-membered alkylene chain or an unsubstituted, 4-membered or 5-membered oxaalkylene chain, the $R_4$s each represent hydrogen and the $R_5$s independently of one another represent hydrogen or the methyl group, or the $R_4$s each represent the methyl group and the $R_5$s each represent hydrogen.

In accordance with a further preference, $R_1$ or $R_1'$ represents an unsubstituted alkyl or alkylidene group having 1 – 8 carbon atoms, a cyclohexyl or cyclohexylidene group or a benzyl or benzylidene group, $R_2$ represents hydrogen or an unsubstituted alkyl group having 1 – 8 carbon atoms, $R_3$ represents hydrogen, an unsubstituted alkyl group having 1 – 8 carbon atoms, or a phenyl, chlorophenyl, furyl, thienyl, pyridyl-3 or pyridyl-4 group, and $R_4$ and $R_5$ each represent hydrogen.

Compounds which are very particularly preferred are those of the formula Ia – Ic wherein $R_1$ and $R_1'$ respectively denote an unsubstituted alkyl or alkylidene group having 1 – 4 carbon atoms, $R_2$ denotes hydrogen or the methyl group, $R_3$ denotes the methyl or phenyl group, and the $R_4$s and $R_5$s each denote hydrogen.

The following may be mentioned as specific compounds which can be prepared by the process according to the invention: (1-n-propyl)-nonatrien-(3,6,8)-yl-n-butylamine, (1-ethyl)-nonatrien-(3,6,8)-yl-n-decylamine, (1-n-butyl)-nonatrien-(3,6,8)-yl-β-methoxyethylamine, (1-isopropyl)-nonatrien-(3,6,8)-yl-γ-methylpropylamine, (1,1-dimethyl)-nonatrien-(3,6,8)-yl-cyclohexylamine, (1-methyl-1-ethyl)-nonatrien-(3,6,8)-yl-tert-butylamine, N-nonatrien-(3,6,8)-yl-benzylamine, (1-methyl)-nonatrien-(3,6,8)-yl-β-N,N-dimethylaminoethylamine, (1-n-decyl)-nonatrien-(3,6,8)-ylβ-phenylethylamine, (1-β-methoxyethyl)-nonatrien-(3,6,8)-yl-isopropylamine, (1-benzyl)-nonatrien-(3,6,8)-yl-cyclopentylamine, [1-(3,3-dimethylbutyl)]-nonatrien-(3,6,8)-yl-methylamine, (1-ethyl)-nonatrien-(3,6,8)-yl-4'-methyl-cyclohexylamine, (1-n-octadecyl)-nonatrien-(3,6,8)-yl-4'-methoxybenzylamine, (1phenyl)-nonatrien-(3,6,8)-yl-n-octylamine, (1-phenyl)-nonatrien-(3,6,8)-yl-β-methylpropylamine, (1-phenyl)-nonatrien-(3,6,8)-yl-tert-butylamine, (1-phenyl)-nonatrien-(3,6,8)-yl-n-dodecylamine, [1-naphthyl-(1)]-nonatrien-(3,6,8)-yl-cyclooctylamine, [1-naphthyl-(2)]-nonatrien-(3,6,8)-yl-n-octadecylamine, [1-(4-methylbenzyl)]-nonatrien-(3,6,8)-yl-ethylamine, [1-(4-chlorophenyl)]-nonatrien-(3,6,8)-yl-isopropylamine, [1-(3,4-dichlorophenyl)]-nonatrien-(3,6,8)-yl-benzylamine, [1-(4-methylaminophenyl)]-nonatrien-(3,6,8)-yl-methylamine, [1-(3-trifluoromethylphenyl)]-nonatrien-(3,6,8)-yl-ethylamine, [1(4-methyl- or 4-methoxyphenyl)]-nonatrien-(3,6,8)-yl-tert-butylamine, (1-β-phenylethyl)-nonatrien-(3,6,8)-yl-n-propylamine, [1-pyridyl(3)- or -pyridyl-(4)]-nonatrien-(3,6,8)-yl-ethylamine, [1-(2,6-dichloropyridyl-4)]-nonatrien-(3,6,8)-yl-methylamine, [1-thienyl-(2)]-nonatrien-(3,6,8)-yl-tert-butylamine, [1-thienyl-(3)]-nonatrien-(3,6,8)-yl-n-octylamine, [1-furyl-(2)]-nonatrien-(3,6,8)-yl-n-propylamine, [1-(5-methylfuryl-(2)]-nonatrien-(3,6,8)-yl-ethylamine, [1-quinolyl-(3)- or -quinolyl-(4)]-nonatrien-(3,6,8)-yl-benzylamine, [1-isoquinolyl- (4)]-nonatrien-(3,6,8)-yl-n-butylamine, [1-(6-methyl-quinolyl-4)]-nonatrien-(3,6,8)-yl-n-butylamine, 1-n-butylamino-1-octatrien-(2,5,7)-yl-cyclohexane, 1-ethyl-1-octatrien-(2,5,7)-yl-tetrahydrofurane-2, 1-n-propyl-1-octatrien-(2,5,7)-yl-tetrahydropyrane 1-tert-butyl-1-octatrien-(2,5,7)-yl-cyclooctane or -cyclodedecane as well as the corresponding saturated compounds.

Compounds of the formula Ib

N-Butylidene-(1-n-propyl)-nonadien-(3,8)-yl-amine, N-methylidene-(1-methyl)-nonadien-(3,8)-yl-amine, N-ethylidene-(1-n-octyl)-nonadien-(3,8)-yl-amine, N-propylidene-(1-ethyl)-nonadien-(3,8)-yl-amine, N-isopropylidene-(1-β-methoxyethyl)-nonadien-(3,8)-yl-amine, N-butylidene-(1-methyl-1n-propyl)-nonadien-(3,8)-yl-amine, N-isopropylidene-(1,1-diethyl)-nonadien-(3,8)-yl-amine, N-tert-butylidene-N-nonadien-(3,8)-yl-amine, N-octylidene-(1-benzyl)-nonadien-(3,8)-yl-amine, N-dodecylidene-(1-n-octyl)-nondien-(3,8)-yl-amine, N-benzylidene[1-(4-methylbenzyl)]-nonadien-(3,8)-yl-amine, N-ethylidene-(1-β-phenylethyl)-nonadien-(3,8)-amine, N-benzylidene-(1-β-methylpropyl)-nonadien-(3,8)-yl-amine, N-benzylidene-(1-benzyl)-nonadien-(3,8)-yl-amine, N-4-chlorobenzylidene-(1-isopropyl)-nonadien-(3,8)-yl-amine, N-4-trifluoromethylbenzylidene-(1-n-butyl)-nonadien-(3,8)-yl-amine, N-3,4-dimethoxybenzylidene-(1,1-dimethyl)-nonadien-(3,8)-yl-amine, N-3-methylbenzylidene-(1-n-octyl)-nonadien-(3,8)-yl-amine, N-α- or N-β-naphthyl-methylene-(1-n-butyl)-nonadien-(3,8)-yl-amine, N-phenethylidene-(1-ethyl)-nonadien-(3,8)-yl-amine, N-4-pyridylidene-(1-methyl)-nonadien-(3,8)-yl-amine, N-2-thenylidene-(1-n-butyl)-nonaien-(3,8) -yl-amine, N-4-quinolylidene-(1-benzyl)-nonadien-(3,8) -yl-amine and N-4-isoquinolylidene-(1-isopropyl)-nonadien-(3,8-yl-amine.

The 1,3-diolefines of the formula II and the Schiff's bases of the formula III, which are used as starting products, are known or can be prepared in a manner which is in itself known.

2-Methyl-butadiene-1,3, 2,3-dimethyl-butadiene-1,3 and hexadiene-2,4, but especially butadiene-1,3, are preferably used as the 1,3-diolefines of the formula II.

The catalysts which can be used in the process according to the invention are in themselves known. It is preferable to use those which are obtained, under reducing conditions, by the action of an electron-donor on compounds of nickel which are free from carbon monoxide, particularly by the reduction of compounds of nickel which are free from carbon monoxide using halogen-free organo-metallic compounds, such as metal alkyls or metal aryls, in the presence of an electron-donor.

Examples of suitable compounds of nickel which are free from carbon monoxide, are nickel acetylacetonate, nickel dimethylglyoxime, nickel formate and dicyclopentadienyl-nickel; nickel acetylacetonate is preferred.

Examples of possible metal alkyls or metal aryls are n-butyl-lithium, methyl-lithium, tri-n-butyl-gallium and diethyl-zinc, but above all trialkyl-aluminium and dialkylalkoxy-aluminium, such as trimethyl-aluminium, triethyl-aluminium, tri-n-butyl-aluminium, tri-n-octyl-aluminium and ethoxydiethyl-aluminium. The use of ethoxydiethyl-aluminium as the reducing agent as proved particularly advantageous.

Lewis bases, such as cyclic ethers, alkylphosphines or arylphosphines, alkyl phosphites or aryl phosphites and the corresponding compounds of arsenic and antimony, for example dioxane, tetrahydrofurane, tetrahydropyrane, triethylphosphine, tricyclohexylphosphine, triphenylphosphine, triethylarsine, triphenylarsine, triphenyl-antimony, triphenyl phosphite, tris-o-cresyl phosphite, tris-o-methoxyphenyl phosphite, o-biphenylyl-diphenyl phosphite and tris-o-biphenylyl phosphite, are employed as the electron-donors (ligands). Triphenylphosphine is preferably used.

The nickel compound and the electron-donor are appropriately used in a mutual molar ratio of 1:1 to about 1:3, whilst the reducing agent is employed in about a 2-fold to 10-fold excess, relative to the nickel compound.

The catalyst is customarily prepared in situ by reducing the carbon monoxide-free nickel compound, optionally in the presence of the electron-donor, in an inert solvent which already contains the starting diolefine of the formula II. The reduction can be carried out here by adding one of the abovementioned reducing agents or by electrolytic means. On the other hand, it is also possible to use a previously isolated nickel O-complex, such as the ethylene-bis-(triphenylphosphine)-nickel O-complex, the bis-cyclooctadiene-(1,5-nickel O-complex or the trans-cyclododecatriene-(1,5,9)-nickel O-complex, for the reaction of the 1,3-diolefine of the formula II with the compound of the formula III. Such nickel O-complex catalysts can be prepared in a known manner, also by the reduction of a carbon monoxide-free compound of nickel in the presence of a suitable olefine and, optionally, a Lewis base.

Examples of basic reaction accelerators which can be employed are monoalkylhydrazines, such as methylhydrazine and n-butylhydrazine, secondary aliphatic or cyclic amines, such as N,N-dimethylamine, N,N-diethylamine, N-methyl-N-n-Propylamine, pyrrolidine, imidazolidine, pyrazolidine, piperidine, piperazine and morpholine, or pyridine and pyridine bases. Morpholine is the preferred reaction accelerator. In general, the reaction accelerators are used in quantity of about 10 to 40 percent by weight, relative to the compound of the formula III.

The reaction according to the invention to give compounds of the formula Ia or Ib is advantageously carried out in the presence of an inert organic solvent. Possible inert organic solvents are especially aliphatic or aromatic hydrocarbons, which are optionally halogenated, or aliphatic and cycloaliphatic ethers, such as n-hexane, n-heptane, benzene, toluene, chlorobenzene, diethyl ether and dioxane. The reaction is very particularly preferentially carried out under anhydrous conditions, above all in anhydrous toluene. However, it is also possible to use an excess of the starting diolefine of the formula II as a solvent, both as early as in the preparation of the catalyst and during the subsequent reaction with the compound of the formula III.

If the reaction is carried out in the presence of an organic solvent, it is possible — without significantly impairing the yields of compound of the formula Ia or Ib — to work both with stoichiometric quantities of the 1,3-diolefine of the formula II and the compound of the formula III, and with a slight excess of the 1,3-diolefine.

The process according to the invention can be carried out at normal pressure or at excess pressure, for example an excess pressure of up to about 10 bars; it is preferable to work at an initial pressure of about 1 to 1.5 bars.

Although the reaction can be carried out at temperatures between −50° C. and +100° C., a temperature range from 20° C to 95° C is preferred. At temperatures below approx. 70° C, especially at temperatures between approx. 20° and 40° C, nonatrien-(3,6,8)-ylamines of the formula Ia and/or nonadien-(3,8)-ylamines of the formula Ib, but especially nonatrien-(3,6,8)-ylamines, are generally formed, depending on the reaction components. The temperature range from 20° C. to 40° C is therefore preferred for the preparation of compounds of the formula Ia. At temperatures above approx. 70° C, on the other hand, nonadien-(3,8)-ylamines of the formula Ib are formed virtually exclusively, in good to very good yields, even without adding a reaction accelerator. Reaction temperatures between 80° and 95° C are therefore particularly preferred for the preparation of compounds of the formula Ib.

In general, it is advisable to carry out the reaction under a protective gas, such as nitrogen or argon. After the completion of the reaction, the catalyst is suitably deactivated, for example by adding triphenyl phosphite to the reaction mixture.

The compounds of the formula Ia or Ib which are produced in the reaction can, if desired, be converted into the corresponding saturated compounds of the formula Ic, in a manner which is in itself known, by hydrogenation, for example by catalytic means, for example using Raney nickel catalysts, palladium-charcoal catalysts (5% Pd) or platinum dioxide. The hydrogenation is appropriately carried out in the presence of a suitable inert organic solvent, such as methanol, ethanol, cyclohexane or dioxane, or mixtures of such solvents. Compounds of the formula Ia can, additionally, be hydrogenated with the addition of anhydrous acetic acid. An increase in the rate of hydrogenation can be achieved by this means.

The nonatrienes and nonadienes of the formula Ia or Ib, prepared in accordance with the invention, can be isolated and purified in a customary manner, for example by means of repeated distillation.

The new nonatrienes, nonadienes and saturated compounds of the formula Ic are colourless to slightly yellowish liquids.

In the following examples, the reactions were carried out under a protective gas (nitrogen or argon).

EXAMPLE 1

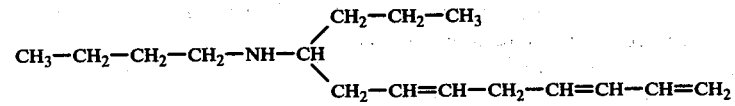

2.3 g (8.94 mmols) of nickel acetylacetonate and 2.25 g (8.56 mmols) of triphenylphosphine are reduced, at 0° to 20° C., in 82 g of absolute toluene in which 35.5 g (0.657 mol) of 1,3-butadiene are dissolved, using 2.65 g (20.35 mmols) of ethoxydiethyl-aluminium. After stirring the reaction mixture for one hour at 20° C., a clear, orange-red catalyst solution is formed. 30.95 g (0.243 mol) of N-butylidene-n-butylamine [boiling point 145°/760 mm Hg] are then added all at once, at 0° C., to the catalyst solution. The reaction mixture is now warmed to 40° C. and kept at this temperature for 20 hours (initial pressure approx. 1.2 bars). The reaction solution is then cooled to 0° C., 10.5 g (33.9 mmols) of triphenyl phosphite are added in order to deactivate the catalyst, and the mixture is distilled. In the course thereof, a 1st fraction is obtained, at a bath temperature of up to 50° C./0.2 mm Hg, which contains (according to gas chromatography) 14.1 g (0.261 mol) that is to say, 39.7% by weight, of unconverted 1,3-butadiene as well as 7.36 g (58mmols) = 23.8% by weight of N-butylidene-n-butylamine and 80 g of toluene. Subsequent refining distillation gives 22.4 g (95.2 mmols) of (1-n-propyl)-nonatrien-(3,6,8)-yl-n-butylamine; yield: 51.2% of theory, relative to N-butylidene-n-butylamine reacted (conversion 76.1%); boiling point 79° C./0.2 mm Hg; $n_D^{25}$ = 1.4727.

Analysis for $C_{16}H_{29}N$: Calculated: C, 81.7%; H, 12.35%; N, 5.95%. Found: C, 81.1%; H, 12.35%; N, 6.2%.

Mass spectrum: molecule peak 235, fragment masses 234, 206, 192, 128, 112 and 72;

$H^1$-NMR spectrum: $\tau$[ppm]: 3.4–5.1(m), 7.0–7.65(m), 7.9(m), 8.65(m), 9.10 (t) in the ratio 7:5:2:8:7;

IR spectrum (liquid): $\nu$(C=C—C=C) — 1650, 1600 $cm^{-1}$; $\delta$ (—CH=CH$_2$) — 900, 1000 $cm^{-1}$;

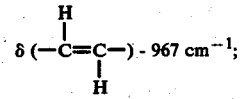

$\delta$ (CH$_3$) — 1375 $cm^{-1}$.

EXAMPLE 2

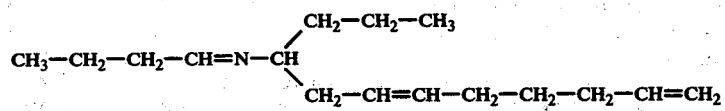

If the procedure is as indicated in Example 1, but the reaction conditions are altered in such a way that the catalysis takes place for 20 hours at 40° C. and for a further 48 hours at 25° C., N-butylidene-(1-n-propyl)-nonadien-(3,8)-ylamine is obtained as the predominant reaction product in a yield of 14% of theory (conversion 100%), boiling point 72° C./0.2 mm Hg; $n_D^{24}$ = 1.4560.

Analysis for $C_{16}H_{29}N$: Calculated: C, 81.7%, H, 12.35%; N, 5.95%. Found: C, 81.54% H, 12.65%, N, 5.86%.

Mass spectrum: molecule peak 235; fragment masses 236, 234, 220, 206, 192, 180, 166, 138, 126;

$H^1$-NMR spectrum: $\tau$ [ppm]: 2.57(t), 4.30(m), 4.72(m), 5.12(m), 7.21(quin), 7.50(m), 7.93 (m), 8.61(m), 9.10(t) in the ratio 1:1:2:2:1:2:6:8:6;

IR spectrum (liquid): $\nu$ (C=N)—1670 $cm^{-1}$; $\nu$(C=C)—1645 $cm^{-1}$; $\delta$(—CH=CH$_2$)—910, 990 $cm^{-1}$;

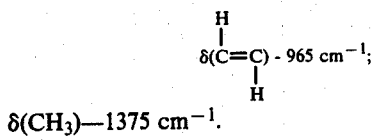

$\delta(CH_3) - 1375\ cm^{-1}$.

EXAMPLE 3

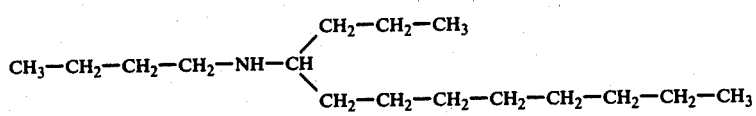

The compounds prepared in accordance with Examples 1 and 2, (1-n-propyl)-nonatrien-(3,6,8)-yl-n-butylamine and N-butylidene-(1-n-propyl)-nonadien-(3,8)-ylamine, which are isomeric in respect of the position of the double bonds, are hydrogenated at normal pressure and room temperature (25° C.) in methanol as solvent, using a Raney nickel catalyst, and with the absorption of 3 mols of hydrogen, in each case, to give (1-n-propyl)-nonyl-n-butylamine; boiling point 78° C./0.2 mm Hg; $n_D^{23}$ — 1.4405.

Analysis for $C_{16}H_{35}N$: Calculated: C, 79.7%; H, 14.5%; N, 5.8%. Found: C, 79.6%; H, 14.4%; N, 5.9%.

Mass spectrum: molecule peak 241, fragment masses 240, 226, 212, 198, 142 and 128;

$H^1$-NMR spectrum: $\tau$ [ppm]: 7.41(m), 8.37(s), 8.70(s), 9.08(t) in the ratio 3:1:22:9.

EXAMPLE 4

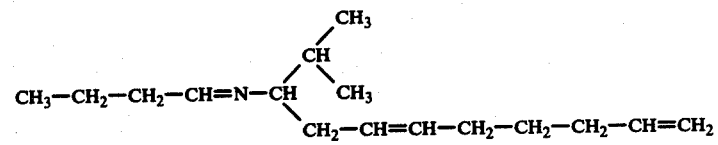

The procedure is as described in Example 1, but using 31.6 g (0.249 mol) of N-isobutylidene-n-butylamine instead of 30.95 g (0.243 mol) of N-butylidene-n-butylamine and 28.6 g (0.529 mol) of 1,3-butadiene. 34.4 g (0.1465 mol) of N-butylidene-(1-isopropyl)-nonadien-(3,8)-ylamine are obtained by means of refining distillation, as described in Example 1; yield 62% of theory, relative to N-isobutylidene-n-butylamine reacted (conversion 95%); boiling point 68–70° C./0.1 mm Hg, $n_D^{24}$ = 1.4564.

Analysis for $C_{16}H_{29}N$: Calculated: C, 81.6%; H, 12.3%; N, 6.0%. Found: C, 81.8%; H, 12.4%; N, 6.0%.

Mass spectrum: molecule peak 235, fragment masses 234, 220, 206, 192, 178, 166, 126 and 67;

$H^1$-NMR spectrum: $\tau$ [ppm]: 2.54(t), 4.20(m), 4.68(n), 5.02 and 5.04(m), 7.44(m), 7.78 and 7.99(m), 8.50(m), 9.0 and 9.1(m) in the ratio 1:1:2:2:1:8:5:9;

IR spectrum (liquid): $\nu(C=N)$ — 1670 cm$^{-1}$; $\nu(C=C)$ — 1640 cm$^{-1}$; $\delta(-CH=CH_2)$ — 910, 990 cm$^{-1}$;

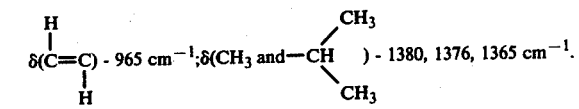

EXAMPLE 5

If, instead of using 2.25 g (8.56 mmols) of triphenylphosphine, no addition at all of this phosphine ligand is made in Example 4, with the procedure being otherwise identical, N-butylidene-(1-isopropyl)-nonadien-(3,8)-ylamine is obtained in a yield of 65.1% of theory, relative to N-isobutylidene-n-butylamine reacted (conversion 97.4%).

EXAMPLE 6

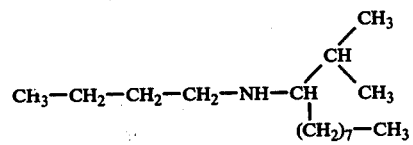

N-Butylidene-(1-isopropyl)-nonadien-(3,8)-ylamine, prepared according to Examples 4 and 5, is hydrogenated in methanol as solvent at normal pressure and room temperature (25° C.) using a Raney nichel catalyst, and with the absorption of 3 mols of hydrogen, to give (1-isopropyl)-nonyl-n-butylamine; boiling point 75° C./02 mm Hg; $n_D^{22}$ = 1.4296

Analysis for $C_{16}H_{35}N$: Calculated: C, 79.7%; H, 14.6%; N, 5.7%. Found: C, 79.5%; H, 14.7%; N, 5.9%.

Mass spectrum: molecule peak 241, fragment masses 240, 226, 212, 198, 142 and 128;

$H^1$-NMR spectrum: $\tau$ [ppm]: 7.52(t), 7.87(q), 8.29(m), 8.75(s), 9.17(d) and (t) in the ratio 2:1:1:19:12.

EXAMPLE 7

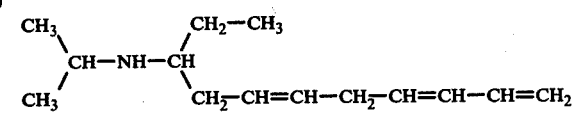

The procedure is as described in Example 1, but using 10.8 g (0.109 mol) of N-propylidene-isopropylamine instead of 30.95 g (0.243 mol) of N-butylidene-n-butylamine, and 14.95 g (0.277 mol) of 1,3-butadiene. Refining distillation, as described in Example 1, gives 12.5 g (60.4 mmols) of (1-ethyl)-nonatrien-(3,6,8)-yl-isopropylamine; yield: 55.4% of theory, relative to N-propylidene-isopropylamine reacted (conversion 100%); boiling point 55° C./02 mm Hg; $n_D^{22}$ = 1.4721.

Analysis for $C_{14}H_{25}N$: Calculated: C, 81.1%; H, 12.1%; N, 6.8%. Found: C, 80.8%; H, 12.4%; N, 6.8%.

Mass spectrum: molecule peak 207, fragment masses 192, 178, and 100;

H¹-NMR spectrum: τ [ppm]: 3.4–4.6(m), 4.66(m), 5.04(m), 7.22(m), 7.55(quin), 7.98(m), 8.65(quin), 9.00(d) and 9.15(t) in the ratio 3:2:2:3:1:2:3:6:3;

IR spectrum (liquid): ν(C=C—C=C)—1650, 1600 cm⁻¹; δ(—CH=CH₂)-900, 1000 cm⁻¹;

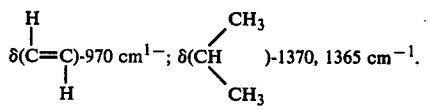

δ(C=C)-970 cm⁻¹; δ(CH⟨CH₃/CH₃⟩)-1370, 1365 cm⁻¹.

EXAMPLE 8

If the procedure is as indicated in Example 7, but without the addition of triphenylphosphine as a ligand, (1-ethyl)-nonatrien-(3,6,8)-yl-isopropylamine is isolated in a yield of 18% of theory (conversion 50.4%).

EXAMPLE 9

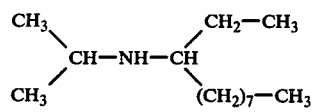

CH₃\
  CH—NH—CH\
CH₃/   \(CH₂)₇—CH₃ , CH₂—CH₃

(1-Ethyl)-nonatrien-(3,6,8)-yl-isopropylamine, prepared in accordance with Examples 7 and 8, on hydrogenation using Raney nickel in ethanol, and with the absorption of 3 mols of hydrogen, gives (1-ethyl)-nonyl-isopropylamine; boiling point 63.5° C/0.2 mm Hg; $n_D^{24}$ = 1.4320.

Analysis for C₁₄H₃₁N: Calculated: C, 78.8%; H, 14.55%; N, 6.55%. Found: C, 78.93%; H, 14.64%; N, 6.54%.

Mass spectrum: molecule peak 213, fragment masses 214, 212, 198, 184, 142 and 100;

H¹-NMR spectrum: τ [ppm]: 7.22(sep), 7.61(quin), 8.75(s), 9.00(d), 9.17(m) in the ratio 1:1:16:6:7.

EXAMPLE 10

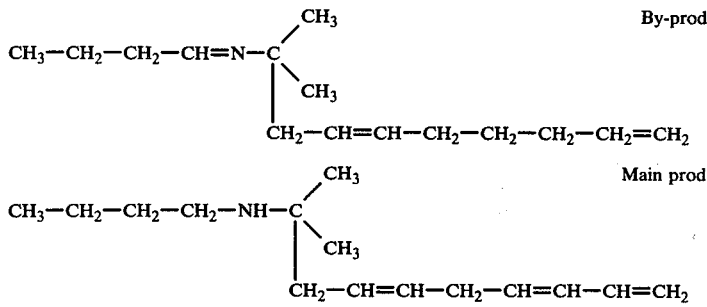

By-product

Main product

The procedure is as described in Example 1, but using 16.85 g (0.149 mol) of N-isopropylidene-n-butylamine instead of 30.95 g (0.243 mol) of N-butylidene-n-butylamine, 20.75 g (0.384 mol) of 1,3-butadiene and without triphenylphosphine as a ligand. After the subsequent distillation, 17.3 g (78.3 mmols) are obtained of a mixture of 39.6% of N-butylidene(1,1-dimethyl)-nonadien- (3,8)-ylamine and 60.4% of (1,1-dimethyl)-nonatrien-(3,6,8)-yl-n-butylamine. The yield of co-oligomerisation products is 50.7% of theory, relative to N-isopropylidene-n-butylamine reacted (conversion 100%); boiling point 60–64° C/0.2 mm Hg; $n_D^{24}$ = 1.4729.

Analysis for C₁₅H₂₇N: Calculated: C, 81.4%; H, 12.15%; N, 6.33%. Found: C, 79.7%; H, 12.2%; N, 6.1%.

Mass spectrum: molecule peak 221, fragment masses 222, 220, 206, 178, 152 and 114 (main product);

H¹-NMR spectrum: (main product) τ [ppm]: 3.3–4.4(m), 4.52(m), 4.92 and 5.01(m), 7.15(q), 7.49(t), 7.92(m), 8.60(m), 8.98(s) and 9.09(t) in the ratio 3:2:2:2:2:2:5:9;

IR spectrum (liquid): (main product) ν(C=C—C=C) — 1650, 1610 cm⁻¹; δ(—CH=CH₂)—905, 1005 cm⁻¹:

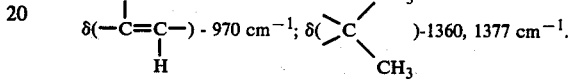

δ(—C=C—)-970 cm⁻¹; δ(C⟨CH₃/CH₃⟩)-1360, 1377 cm⁻¹.

EXAMPLE 11

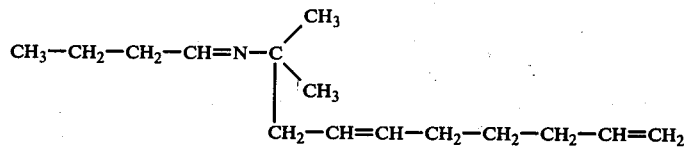

CH₃—CH₂—CH₂—CH=N—C⟨CH₃/CH₃⟩
                      |
                      CH₂—CH=CH—CH₂—CH₂—CH₂—CH=CH₂

The procedure is as described in Example 10, but using 2.25 g (8.56 mmols) of triphenylphosphine as a ligand. This gives, as the exclusive product, the by-product formed in Example 10, namely N-butylidene-(1,1-dimethyl)-nonadien-(3,8)-ylamine; yield 27.1% of theory, relative to N-isopropylidene-n-butylamine reacted (conversion 100%); boiling point 60–62° 0/0.2 mm Hg; $n_D^{24}$ = 1.4624.

Analysis for C₁₅H₂₇N: Calculated: C, 81.4%; H, 12.15%; N, 6.33%. Found: C, 80.0%; H, 12.1%; N, 6.2%.

Mass spectrum: molecule peak 221, fragment masses 222, 220, 206, 178, 152, 112 and 95;

H¹-NMR spectrum: τ [ppm]: 2.5(t), 4.1–4.7(m), 4.95 and 5.19(m), 7.5–8.1(m), 8.2–8.7(m), 8.87(s) and 9.1(t) in the ratio 1:3:2:8:4:9;

IR spectrum (liquid): ν(C=N) — 1675 cm⁻¹; ν(C=C) — 1650 cm⁻¹; δ(—C=CH₂) - 910, 990 cm⁻¹;

$\delta(-\overset{H}{\underset{H}{C}}=\overset{}{\underset{}{C}}-) - 972\ cm^{-1};\ \delta(\overset{CH_3}{\underset{CH_3}{>}}C\overset{}{\underset{}{<}}) - 1365, 1380\ cm^{-1}.$

EXAMPLE 12

$CH_3-CH_2-CH_2-CH_2-NH-\underset{\underset{(CH_2)_7-CH_3}{|}}{\overset{CH_3}{\underset{CH_3}{C<}}}$ The compounds prepared in accordance with Examples 10 and 11, namely (1,1-dimethyl)-nonatrien-(3,6,8)-yl-n-butylamine and N-butylidene-(1,1-dimethyl)-nonadien-(3,8)-ylamine, on hydrogenation in methanol using a Raney nickel catalyst, and with the absorption of 3 mols of hydrogen in each case, give (1,1-dimethyl)-nonyl-n-butylamine; boiling point 67° C/0.1 mm Hg; $n_D^{24} = 1.4382$.

Analysis for $C_{15}H_{33}N$: Calculated: C, 79.3%; H, 14.55%; N, 6.15%. Found: C, 79.21%; H, 14.77%; N, 6.03%.

Mass spectrum: molecule peak 227, fragment masses 226, 212, 184, 156, 142 and 114;

$H^1$-NMR spectrum: $\tau$ [ppm]: 7.57(t), 8.75(s), 8.96 and 9.00 in each case (s), 9.15(t) in the ratio 2:19:6:6.

EXAMPLE 13

$\overset{CH_3}{\underset{CH_3}{>}}C=N-CH-\underset{\underset{CH_2-CH=CH-CH_2-CH_2-CH_2-CH=CH_2}{|}}{CH<}\overset{CH_3}{\underset{CH_3}{}}$ The procedure is as described in Example 1, but using 28.3 g (0.2505 mol) of N-isobutylidene-isopropylamine instead of 30.95 g (0.243 mol) of N-butylidene-n-butylamine. A refining distillation gives 14.0 g (63.2 mmols) of N-isopropylidene-(1-isopropyl)-nonadien-(3,8)-ylamine; yield 50.2% of theory, relative to N-isobutylidene-isopropylamine reacted (conversion 50.4%); boiling point 56° C/0.2 mm Hg; $n_D^{23} = 1.4586$.

Analysis for $C_{15}H_{27}N$: Calculated: C, 81.4%; H, 12.2%; N, 6.34%. Found: C, 81.23%; H, 12.48%; N, 6.29%.

Mass spectrum: molecule peak 221, fragment masses, 222, 220, 206, 178, 152, 136, 122 and 112;

$H^1$-NMR spectrum: $\tau$ [ppm] 4.30(m), 4.76(m), 5.14(m), 7.01(m), 7.7–8.1(m) 8.06(s), 8.30(s), 8.60(m), 9.14 and 9.21(dd) in the ratio 1:2:2:1:6:3:3:3:6;

IR spectrum (liquid: $\nu(C=N)$ — 1650 $cm^{-1}$; $\nu(C=C)$ — 1640 $cm^{-1}$; $\delta(-CH=CH_2)$ — 910, 990 $cm^{-1}$;

$\delta(\overset{H}{\underset{H}{C}}=C) - 970\ cm^{-1};\ \delta(\overset{CH_3}{\underset{CH_3}{>}}C\overset{}{\underset{}{<}}) - 1670, 1685\ cm^{-1}.$

EXAMPLE 14

The procedure is as described in Example 13, but without the addition of triphenylphosphine. N-iso-propylidene-(1-isopropyl)-nonadien-(3,8)-ylamine is obtained in a yield of 19.3% of theory, relative to N-isobutylidene-isopropylamine reacted (conversion 32.7%).

EXAMPLE 15

$\overset{CH_3}{\underset{CH_3}{>}}CH-NH-CH-\underset{\underset{(CH_2)_7-CH_3}{|}}{CH<}\overset{CH_3}{\underset{CH_3}{}}$ N-isopropylidene-(1-isopropyl)-nonadien-(3,8)-ylamine prepared in accordance with Examples 13 and 14, on hydrogenation using Raney nickel in methanol, and with the absorption of 3 mols of hydrogen, gives (1-isopropyl)-nonyl-isopropylamine; boiling point 57.5° C/0.1 mm Hg; $n_D^{24} = 1.4384$.

Analysis for $C_{15}H_{33}N$: Calculated: C, 79.3%; H, 14.55%; N, 6.17%. Found: C, 78.62%; H, 14.79%; N, 6.49%.

Mass spectrum: molecule peak 227, fragment masses 228, 226, 212, 184, 168, 142, 114, 98, 72 and 56;

$H^1$-NMR spectrum: $\tau$ [ppm]: 7.58(m), 8.75(s), 9.02(d), 9.14 and 9.17(dd) in the ratio 2:16:15

EXAMPLE 16

$\underset{\underset{CH_3}{|}}{\overset{\overset{CH_3}{|}}{CH_3-C}}-NH-CH_2-CH_2-CH=CH-CH_2-CH=CH-CH=CH_2$ The procedure is as described in Example 1, but using 18.65 g (0.2195 mol) of N-methylidene-tert-butylamine instead of 30.95 g (0.243 mol) of N-butylidene-n-butylamine. A refining distillation gives 5.43 g (28.2 mmols) of N-nonatrien-(3,6,8)-yl-tert-butylamine; yield 19.6% of theory, relative to N-methylidene-tert-butylamine reacted (conversion 65.9%); boiling point 52° C/0.2 mm Hg; $n_D^{23} = 1.4740$.

Analysis for $C_{12}H_{23}N$: Calculated: C, 80.4%; H, 11.7%; N, 7.9%. Found: C, 78.2%; H, 12.0%; N, 7.9%.

Mass spectrum: molecule peak 193, fragment masses 194, 178, 154, 121, 114, 105, 86, 57, 41 and 30;

$H^1$-NMR spectrum: $\tau$ [ppm]: 3.4–4.6(m), 4.63(m), 4.99 and 5.04(m), 7.24(m), 7.47(t), 7.91(m), 8.68(s), 8.94(s) in the ratio 3:2:2:2:2:2:1:9;

IR spectrum (liquid): $\nu(C=C-C=C)$—1650, 1605 $cm^{-1}$; $\delta(C=C-CH=CH_2)$—900, 1005 $cm^{-1}$;

$\delta(\overset{H}{\underset{H}{C}}=C) - 972\ cm^{-1};\ \delta(\overset{CH_3}{\underset{CH_3}{>}}C-CH_3) - 1360, 1385\ cm^{-1}$

EXAMPLE 17

$CH_3-NH-\underset{\underset{CH_2-CH=CH-CH_2-CH=CH-CH=CH_2}{|}}{CH}-\bigcirc$

The procedure followed is as in Example 1, but using 33.0 g (0.277 mol) of N-benzylidene-methylamine instead of 30.95 g (0.243 mol) of N-butylidene-n-butylamine, and 29.8 g (0.551 mol) of 1,3-butadiene. A refining distillation gives 18.5 g (31.5 mmols) of (1-phenyl)-nonatrien-(3,6,8)-yl-methylamine; yield 35.3% of theory, relative to N-benzylidenemethylamine reacted (conversion 82.6%); boiling point 76–78° C./0.001 mm Hg; $n_D^{23.5} = 1.5376$.

Analysis for $C_{16}H_{21}N$: Calculated: C, 84.5%; H, 9.3%; N, 6.2%. Found: C, 83.7%; H, 9.4%; N, 6.1%.

Mass spectrum: molecule peak 227, fragment masses 212, 120, 103 and 91;

$H^1$-NMR spectrum: $\tau$ [ppm]: 2.82(s), 3.64 and 4.38(m), 4.66(m), 4.87 and 5.01(m), 6.59(t), 7.28(m), 7.69(m), 7.80(s), 8.02(s) in the ratio 5:3:2:2:1:2:2:3:1;

IR spectrum (liquid):

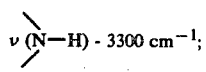

$\nu$ (N—H) - 3300 cm$^{-1}$;

$\nu$ (C=C—C=C) — 1645, 1605 cm$^{-1}$; $\delta$ (—CH=CH$_2$) — 902, 1005 cm$^{-1}$;

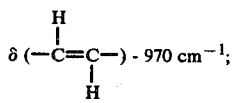

$\delta$ (—C=C—) - 970 cm$^{-1}$;

$\delta$ (—CH$_3$) — 1355 cm$^{-1}$.

EXAMPLE 18

If triphenylphosphine is not used in Example 17, an otherwise identical procedure gives (1-phenyl)-nonatrien(3,6,8)-yl-methylamine in a yield of 13.4% of theory, relative to N-benzylidene-methylamine reacted (conversion 75%).

EXAMPLE 19

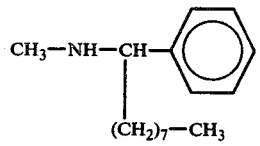

The (1-phenyl)-nonatrien-(3,6,8)-yl-methylamine, prepared in accordance with Examples 17 and 18, is hydrogenated in methanol at normal pressure and room temperature (25° C), using a Raney nickel catalyst, and with the absorption of 3 mols of hydrogen, to give (1-phenyl)-nonyl-methylamine; boiling point 98° C/0.1 mm Hg; $n_D^{23} = 1.5164$.

Analysis for $C_{16}H_{27}N$: Calculated: C, 82.36%; H, 11.66%; N, 6.0%. Found: C, 82.22%; H, 11.98%; N, 5.99%.

Mass spectrum: molecule peak 233, fragment masses 232, 160, 156, 134, 120, 91 and 42;

$H^1$-NMR spectrum: $\tau$ [ppm]: 2.75(s), 6.57(t), 7.75(s), 8.37(s), 8.75(s), 9.13(t) in the ratio 5:1:3:1:14:3.

EXAMPLE 20

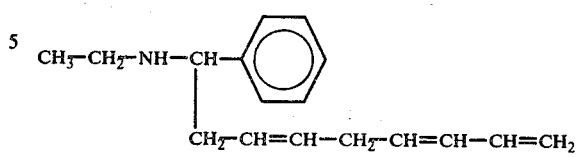

The procedure is as described in Example 1, but using 33.3 g (0.25 mol) of N-benzylidene-ethylamine instead of 30.95 g (0.243 mol) of N-butylidene-n-butylamine, and 26.15 g (0.483 mol) of 1,3-butadiene. After distillation, 9.5 g (39.4 mmols) are obtained of (1-phenyl)-nonatrien-(3,6,8)-yl-ethylamine; yield 20.5% of theory, relative to N-benzylidene-ethylamine reacted (conversion 76.7%); boiling point 86–89° C./0.1 mm Hg; $n_D^{23} = 1.5337$.

Analysis for $C_{17}H_{23}N$: Calculated: C, 84.5%; H, 9.6%; N, 5.85%. Found: C, 83.8%; H, 9.7%; N, 5.6%.

Mass spectrum: molecule peak 241, fragment masses 242, 240, 226, 134, 106 and 91;

$H^1$-NMR spectrum: $\tau$ [ppm]: 2.72(s), 3.6–5.2(m), 6.35(t), 7.25(m), 7.55(m), 7.95(m), 8.40(s), 8.97(t) in the ratio 5:7:1:2:2:2:1:3;

IR spectrum (liquid): $\nu$ (>N—H) — 3300 cm$^{-1}$; $\nu$ (C=C—C=C) — 1645, 1600 cm$^{-1}$; $\delta$ (—CH=CH$_2$) — 907, 1000 cm$^{-1}$;

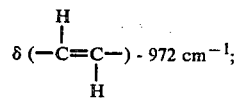

$\delta$ (—C=C—) - 972 cm$^{-1}$;

$\delta$ (—CH$_3$) — 1380 cm$^{-1}$.

EXAMPLE 21

If triphenylphosphine is not used in Example 20, an otherwise identical procedure gives (1-phenyl)-nonatrien-(3,6,8)-yl-ethylamine in a yield of 30.3% of theory, relative to N-benzylidene-ethylamine reacted (conversion 62.5%).

EXAMPLE 22

The procedure is as described in Example 20, but using 73.8 g (0.565 mol) instead of 33 g (0.25 mol) of N-benzylidene-ethylamine, and 57.3 g (1.06 mols) of 1,3-butadiene. 28.8 g (0.331 mol) of morpholine are added to the reaction mixture, which is warmed to 40° C. and kept at this temperature for 2 hours. After deactivating the nickel catalyst by means of triphenyl phosphite, 85.7 g (0.356 mol) of (1-phenyl)-nonatrien-(3,6,8)-yl-ethylamine are obtained by distillation; yield 75% of theory, relative to N-benzylidene-ethylamine reacted (conversion 85.6%).

EXAMPLE 23

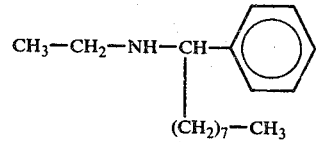

The (1-phenyl)-nonatrien-(3,6,8)-yl-ethylamine, prepared in accordance with Examples 20, 21 and 22, is hydrogenated in methanol at normal pressure and room temperature (25° C.), using a Raney nickel catalyst and with the absorption of 3 mols of hydrogen, to give (1-phenyl)-nonylethylamine; boiling point 90–93° C./0.01 mm Hg; $n_D^{25} = 1.4865$.

Analysis for $C_{17}H_{29}N$: Calculated: C, 82.5%; H, 11.75%; N, 5.67%. Found: C, 82.69%; H, 11.85%; N, 5.70%.

Mass spectrum: molecule peak 247, fragment masses 246, 218, 170, 134, 104 and 91;

$H^1$-NMR spectrum: $\tau$ [ppm]: 2.83(s), 6.53(t), 7.61(9), 8.39(m), 8.81(s), 9.00(t) and 9.17(t) in the ratio 5:1:2:2:13:3:3.

EXAMPLE 24

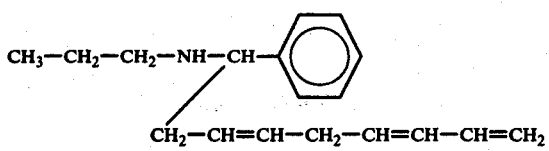

The procedure is as described in Example 1, but using 34.2 g (0.2325 mol) of N-benzylidene-n-propylamine instead of 30.95 g (0.243 mol) of N-butylidene-n-butylamine, and 26.7 g (0.494 mol) of 1,3-butadiene. After distillation, 17.5 g (68.6 mmols) of (1-phenyl)-nonatrien-(3,6,8)-yl-n-propylamine are obtained; yield 37.8% of theory, relative to N-benzylidene-n-propylamine reacted (conversion 77.9%); boiling point 101–104° C./0.001 mm Hg; $n_D^{23} = 1.5282$.

Analysis for $C_{18}H_{25}N$: Calculated: C, 84.6%; H, 9.9%; N, 5.5%. Found: C, 83.5%; H, 9.9%; N, 5.4%.

Mass spectrum: molecule peak 255, fragment masses 254, 226, 213, 198, 186, 148, 106 and 91;

$H^1$-NMR spectrum: $\tau$ [ppm]: 2.78(s), 3.6–5.2(m), 6.40(t), 7.30(m), 7.55(m), 7.95(m), 8.50(m), 9.08(t) in the ratio 5:7:1:2:2:2:3:3;

IR spectrum (liquid): $\nu$ ($>$N—H) — 3300 $cm^{-1}$; $\nu$ (C=C—C=C) — 1650, 1600 $cm^{-1}$; $\delta$ (—CH=CH$_2$) — 905, 998 $cm^{-1}$;

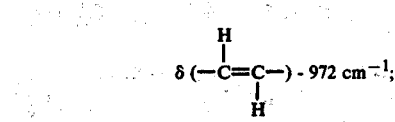

$\delta$ (—CH$_3$) — 1380 $cm^{-1}$.

EXAMPLE 25

If triphenylphosphine is not used in Example 24, an otherwise identical procedure gives (1-phenyl)-nonatrien-(3,6,8)-yl-n-propylamine in a yield of 33.0% of theory, relative to N-benzylidene-n-propylamine reacted (conversion 69%).

EXAMPLE 26

The procedure is as described in Example 22, but using 79.7 g (0.5425 mol) of N-benzylidene-n-propylamine instead of 73.8 g (0.565 mol) of N-benzylidene-ethylamine, and 60.2 g (1.115 mols) of 1,3-butadiene. The subsequent distillation gives 97.5 g of (1-phenyl)-nonatrien-(3,6,8)-yl-n-propylamine; yield 84.5% of theory, relative to N-benzylidene-propylamine reacted (conversion 83.5%).

EXAMPLE 27

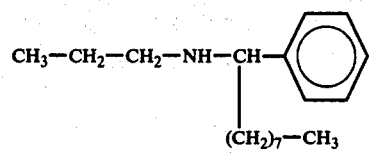

The (1-phenyl)-nonatrien-(3,6,8)-yl-n-propylamine, prepared in accordance with Examples 24, 25 and 26, is hydrogenated in methanol at normal pressure and room temperature (25° C), using a Raney nickel catalyst and with the absorption of 3 mols of hydrogen, to give (1-phenyl)-nonyln-propylamine; boiling point 106–108° C./0.001 mm Hg; $n_D^{24} = 1.4846$.

Analysis for $C_{18}H_{31}N$: Calculated: C, 82.8%; H, 11.87%; N, 5.36%. Found: C, 82.6%; H, 11.7%; N, 5.3%.

Mass spectrum: molecule peak 261, fragment masses 260, 232 and 148;

$H^1$-NMR spectrum: $\tau$ [ppm]: 2.75(s), 6.41(t), 7.59(t), 8.36(m), 8.78(s), 9.14(t) in the ratio 5:1:2:2:14:7.

EXAMPLE 28

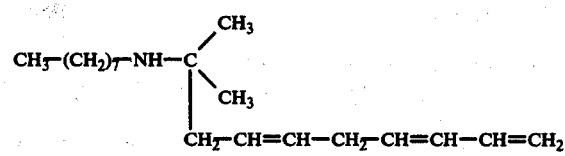

The procedure is as described in Example 1, but using 35.5 g (0.21 mol) of N-isopropylidene-n-octylamine instead of 30.95 g (0.243 mol) of N-butylidene-n-butylamine, and 35.2 g (0.652 mol) of 1,3-butadiene. Distillation gives 21.6 g (78 mmols) of (1,1-dimethyl)-nonatrien(3,6,8)-yl-n-octylamine; yield 44.9% of theory, relative to N-isopropylidene-n-octylamine reacted (conversion 82.9%); boiling point 103–105° C/0.001 mm Hg; $n_D^{23} = 1.4797$.

Analysis for $C_{19}H_{35}N$: Calculated: C, 82.3%; H, 12.65%; N, 5.05%. Found: C, 81.9%; H,12.45%; N, 4.94%.

Mass spectrum: molecule peak 277, fragment masses 278, 276, 262, 225, 217, 170 and 58;

$H^1$-NMR spectrum: $\tau$ [ppm]: 3.3–5.1(m), 7.18(m), 7.51(t), 7.94(m), 8.60(m), 8.99(s) and 9.10(t) in the ratio 7:2:2:2:13:9;

IR spectrum (liquid): $\nu$ (C=C—C=C) — 1645, 1600 $cm^{-1}$; $\delta$ (—CH=CH$_2$) — 900, 1000 $cm^{-1}$;

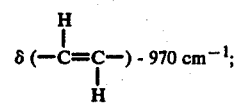

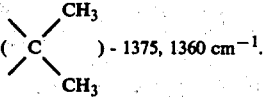

EXAMPLE 28 a

Hydrogenation, as specified in Example 27, of the (1,1-dimethyl)-nonatrien-(3,6,8)-yl-octylamine obtained in accordance with Example 28 gives (1,1-dimethyl)- nonyl-n-octylamine; boiling point 107–108° C./0.01 mm Hg; $n_D^{20} = 1.4444$.

Analysis for $C_{19}H_{41}N$: Calculated: C, 80.50%; H, 14.5%; N, 4.95%. Found: C, 80.2%; H, 14.3%; N, 4.8%.

EXAMPLE 29

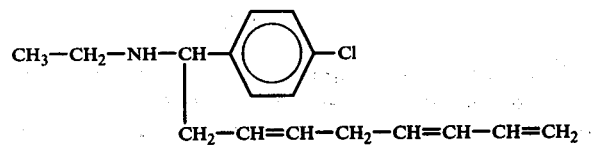

The procedure is as described in Example 1, but using 42.1 g (0.251 mol) of N-4-chlorobenzylidene-ethylamine instead of 30.95g (0.243 mol) of N-butylidene-n-butylamine, and 34.6 g (0.641 mol) of 1.3-butadiene. Distillation gives 11.5 g (41.9 mmols of [1-(4-chlorophenyl)]-nonatrien-(3,6,8)-yl-ethylamine; yield 22.5% of theory, relative to N-4-chlorobenzylidene-ethylamine reacted (conversion 74.1%); boiling point 99–102° C./0.001 mm Hg; $n_D^{25} = 1.5335$.

Analysis for $C_{17}H_{22}NCl$: Calculated: C, 74.1%; H, 7.99%; N, 5.07%; Cl, 12.9%. Found: C, 73.6%; H, 8.1%; N, 4.8% Cl, 12.8%.

Mass spectrum: molecule peak 275, fragment masses 168, 140;

$H^1$-NMR spectrum: $\tau$ [ppm]: 2.80(s), 3.3–5.1(m), 6.46(t), 7.24(m), 7.54(q), 7.70(m), 8.37(s), 8.95(t) in the ratio 4:7:1:2:2:2:1:3;

IR spectrum (liquid(: $\nu$ (>N—H) — 3300 cm$^{-1}$;$\nu$ (C=C—C=C) — 1645, 1600 cm$^{-1}$; $\delta$ (—CH=CH$_2$) — 905, 1000 cm$^{-1}$;

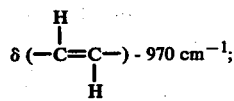

$\delta$ (CH$_3$) — 1375 cm$^{-1}$.

EXAMPLE 30

If triphenylphosphine is not used in Example 29, an otherwise identical procedure gives [1-(4-chlorophenyl)]-nonatrien-(3,6,8)-yl-ethylamine in a yield of 10.3% of theory, relative to N-4-chlorobenzylidene-ethylamine reacted (conversion 50.1%).

EXAMPLE 31

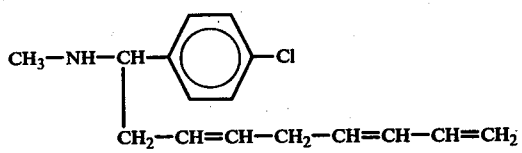

The procedure is as described in Example 22, but using 72.9 g (0.476 mol) of N-4-chlorobenzylidene-methylamine, 69.7 g (1.295 mol) of 1,3-butadiene and 48.6 g (0.558 mol) of morpholine (reaction time: 2 hours at 40° C). The subsequent distillation gives 38.6 g(0.148 mol) of [1-(4-chlorophenyl)]-nonatrien-(3,6,8)-yl-methylamine; yield 32.5% of theory, relative to N-4-chlorobenzylidene-methylamine reacted (conversion 81.5%); boiling point 93–96° C./0.001 mm Hg; $n_D^{24} = 1.5473$.

Analysis for $C_{16}H_{20}NCl$: Calculated: C, 73.5%; H, 7.65%; N, 5.36%; Cl, 13.55%. Found: C, 73.03%; H, 7.80%; N, 5.40%; Cl, 12.82%.

Mass spectrum: molecule peak 261, fragment masses 260, 246, 154;

$H^1$-NMR spectrum: $\tau$ [ppm]: 2.83(s), 3.3–4.65(m), 4.68(m), 4.99 and 5.10(m), 6.60(t), 7.25(m), 7.78(m) and 7.80(s), 8.53(s) in the ratio 4:3:2:1:2:5:1;

IR spectrum (liquid): $\nu$ (>N—H) — 3330 cm$^{-1}$; $\nu$ (C=C—C=C) — 1640, 1600 cm$^{-1}$; $\delta$ (—CH=CH$_2$) — 900, 1005cm$^{-1}$;

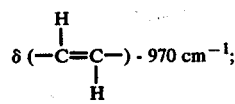

EXAMPLE 32

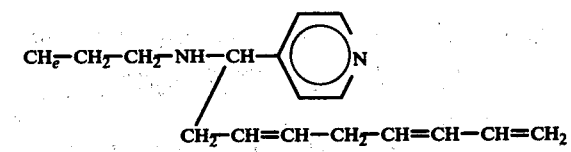

The procedure is as described in Example 1, but using 37.7 g (0.255 mol) of N-4-pyridylidene-n-propylamine instead of 30.95 g (0.243 mol) of N-butylidene-n-butylamine, and 27.6 g (0.511 mol) of 1,3-butadiene. Distillation gives 23.2 g (90.5 mmols) of [1-pyridyl-(4)]-nonatrien-(3,6,8)-yl-n-propylamine. Yield 38.2% of theory, relative to N-(4-pyridylidene)-n-propylamine reacted (conversion 93%); boiling point 110-113° C/0.001 mm Hg; $n_D^{22} = 1.5347$.

Analysis for $C_{17}H_{24}N_2$: Calculated: C, 79.6%; H, 9.37%; N, 10.95%. Found: C, 78.98%; H, 3,38%; N, 10.65%.

Mass spectrum: molecule peak 256, fragment masses 255, 241, 227 and 149;

$H^1$-NMR spectrum: $\tau$ [ppm]: 1.4(m), 2.7(m), 3.3–5.1(m), 6.4(t), 7.35–7.65(m), 7.95(m), 8.5(m), 9.05(t) in the ratio 2:2:7:1:4:2:3:3;

IR spectrum (liquid): $\nu$ (>NH) — 3300 cm$^{-1}$; $\nu$ (C=C—C=C) — 1650, 1600 cm$^{-1}$; $\epsilon$ (—CH=CH$_2$) — 905, 995 cm$^{-1}$;

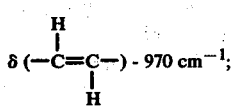

$\delta$ (—CH$_3$) — 1380 cm$^{-1}$.

EXAMPLE 33

If triphenylphosphine is not used in Example 32, an otherwise identical procedure gives [1-pyridyl-(4)]-nonatrien-(3,6,8)-yl-n-propylamine in a yield of 16.0% of theory, relative to N-4-pyridylidene-n-propylamine reacted (conversion 77.5%).

EXAMPLE 34

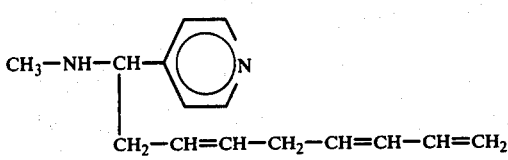

The procedure is as described in Example 22, but using 79.1 g (0.659 mol) of N-4-pyridylidene-methylamine, 64.5 g (1.195 mols) of 1.3-butadiene and 49.25 g (0.566 mol) of morpholine (reaction time 2 hours at 40° C). Distillation gives 83.2 g (0.365 mol) of [1-pyridyl-(4)]-nonatrien(3,6,8)-yl-methylamine; yield 65.9% of theory, relative to N-4-pyridylidene-methylamine reacted (conversion 84.3%); boiling point 108-111° C./0.001 mm Hg; $n_D^{24} = 1.5440$.

Analysis for $C_{19}H_{20}N_2$: Calculated: C, 78.9%; H, 8.76%; N, 12.25%. Found: C, 78.8%; H, 8.8%; N, 11.9%.

Mass spectrum: molecule peak 228, fragment masses 227, 121;

$H^1$-NMR spectrum: $\tau$ [ppm]: 1.54(d), 2.88(d), 3.3-4.6(m), 4.68(m), 5.00 and 5.12(m), 6.58(t), 7.28(m), 7.78(m) and 7.80(s), 8.55(s) in the ratio 2:2:3:2:2:1:2:5:1;

IR spectrum (liquid): $\nu$ (>N-H) — 3300 cm$^{-1}$; $\nu$(C=C—C=C) — 1650, 1600 cm$^{-1}$; $\delta$ (—CH=CH$_2$) — 903, 1005 cm$^{-1}$;

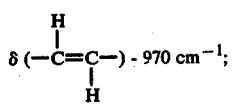

$\delta$ (—CH$_3$) — 1358 cm$^{-1}$.

EXAMPLE 35

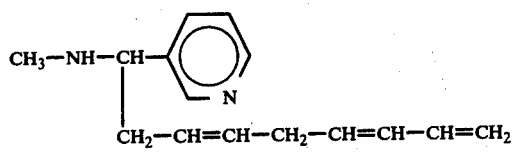

The procedure is as described in Example 1, but using 32.8 g (0.273 mol) of N-m-pyridylidene-methylamine instead of 30.95 g (0.243 mol) of N-butylidene-n-butylamine, and 32.0 g (0.593 mol) of 1,3-butadiene. The subsequent distillation gives 18.5 g (81.0 mmols) of (1-m-pyridyl)-nonatrien-(3,6,8)-yl-methylamine; yield 47.4% of theory, relative to N-m-pyridylidene-methylamine reacted (conversion 64.1%); boiling point of 96-99° C./0.001 mm Hg; $n_D^{20} = 1.5456$.

Analysis for $C_{15}H_{20}N_2$: Calculated C, 79.0%; H, 8.8%; N, 12.2%. Found: C, 78.0%; H, 8.9%; N, 11.8%.

Mass spectrum: molecule peak 228, fragment masses 161, 121 and 94;

$H^1$-NMR spectrum: $\tau$ [ppm]: 1.57(s), 2.45(d), 2.88(m), 3.3–4.65(m), 4.70(m), 5.00(m), 6.54(t), 7.29(m), 7.72(m) and 7.80(s), 8.40(s) in the ratio 2:1:1:3:2:2:1:2:5:1;

IR spectrum (liquid): $\nu$ (>N—H) — 3300 cm$^{-1}$; $\nu$ (C=C—C=C) — 1650, 1600 cm$^{-1}$; $\delta$ (—CH=CH$_2$) — 905, 1005 cm$^{-1}$;

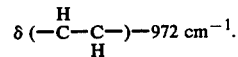

EXAMPLE 36

The procedure is as described in Example 22, but using 29.8 g (0.248 mol) of N-m-pyridylidene-methylamine, 38.7 g (0.716 mol) of 1,3-butadiene and 28.9 g (0.332 mol) of morpholine. Distillation gives 22.9 g (0.1005 mol) of (1-m-pyridyl)-nonatrien(3,6,8)-yl-methylamine; yield 48.8% of theory, relative to N-m-pyridylidene-methylamine reacted (conversion 83.5%).

EXAMPLE 37

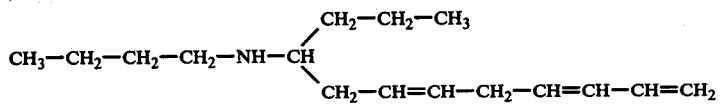

The procedure is as described in Example 22, but using 69.4 g (0.546 mol) of N-butylidine-n-butylamine instead of 73.8 g (0.565 mol) of N-benzylidene-ethylamine, 73.3 g (1.36 mols) of 1,3-butadiene and 30.0 g (0.345 mol) of morpholine. Distillation gives 54.9 g (0.234 mol) of (1-n-propyl-nonatrien-3,6,8)-yl-n-butylamine; yield 49.6% of theory, relative to N-butylidene-n-butylamine reacted (conversion 86.2%).

The physical data of the reaction product are quoted in Example 1.

EXAMPLE 38

If, in Example 37, instead of using 2.25 g (8.56 mmols) of triphenylphosphine, no addition of this phosphine liqand is made, an otherwise identical procedure give (1-n-propyl)-nonatrien-(3,6,8)-yl-n-butylamine in ayield of 2.12% of theory, relative to N-butylidene-n-butylamine reacted (conversion 82.2%).

EXAMPLE 39

2.75 g (10 mmols) of bis-cyclooctadiene-1,5-nickel-(0) and 2.62 g (10 mmols) of triphenylphosphine are dissolved at −10 to 0° C. in 200 ml of absolute benzene containing 54 g (1 mol) of 1,3-butadiene. A clear, homogeneous, orange-red solution is formed. 50 g (0.394 mol) of N-butylidene-n-butylamine are then added and the reaction mixture is stirred at 40° C. for 20 hours. After working up the reaction product as directed in Example 1, (1-n-propyl)-nonatrien-(3,6,8)-yl-n-butylamine is obtained in virtually the same yield as that indicated in Example 1.

EXAMPLE 40

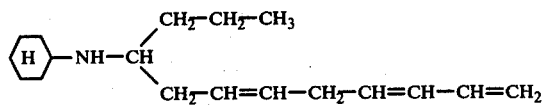

The procedure is as described in Example 1, but using 108 g (0.77 mol) of N-butylidene-cyclohexylamine instead of 30.95 g (0.243 mol) of N-butylidene-n-butylamine, and 83.6 g (1.55 mols) of 1,3-butadiene. The subsequent distillation gives 66.0 g (0.253 mol) of (1-n-propyl)-nonatrien-(3,6,8)-yl-cyclohexylamine; yield 51.1% of theory, relative to N-butylidene-cyclohexylamine reacted (conversion 70.2%); boiling point 90–95° C./0.001 mm Hg; $n_D^{20}$ = 1.4963.

Analysis for $C_{18}H_{31}N$: Calculated: C, 82.7 %; H, 11.9%; N, 5.4%. Found: C, 82.5%; H, 12.2%; N, 5.6%.

Mass spectrum: molecule peak 261, fragment masses 260, 218, 192, 178, 154 and 72;

$H^1$-NMR spectrum: τ [ppm]: 3.3 – 4.6(m), 4.63(m), 4.86 and 5.10(m), 7.24(m), 7.53(m), 7.96(m), 8.27(m), 8.70(m), 8.88(s), 9.12(t) in the ratio 3:2:2:2:2:2:5:9:1:3;

IR spectrum (liquid): ν (c=C—C=C) — 1650, 1600 $cm^{-1}$; δ (—CH=$CH_2$) — 900, 1000 $cm^{-1}$;

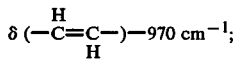

δ (—$CH_3$) — 1370 $cm^{-1}$.

EXAMPLE 41

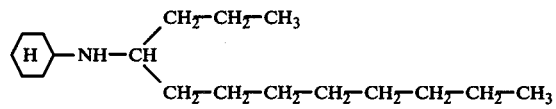

The (1-n-propyl)-nonatrien-(3,6,8)-yl-cyclohexylamine, prepared in accordance with Example 40, is hydrogenated at normal pressure and room temperature (25° C.), using a palladium-charcoal catalyst in a mixture of glacial acetic acid/methanol (volume ratio 1:3) , and with the absorption of 3 mols of hydrogen, to give (1-n-propyl)-nonyl-cyclohexylamine; boiling point 104 – 106° C/0.001 mm Hg; $n_D^{23}$ = 1.4586.

Analysis for $C_{18}H_{37}N$: Calculated: C, 80.9%; H, 13.9%; N, 5.2%. Found: C, 81.0%; H, 13.9%; N, 5.0%.

Mass spectrum: molecule peak 267, fragment masses 266, 252, 224 and 154;

$H^1$-NMR spectrum: τ [ppm]: 7.56(m), 8.26(m), 8.74(s), 9.13(t) in the ratio 2:6:22:7.

EXAMPLE 42

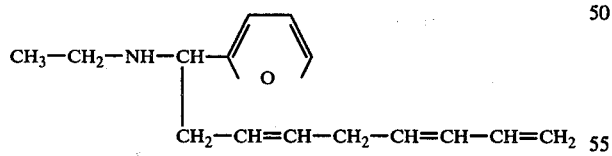

The procedure is as described in Example 1, but using 30.35 g (0.247 mol) of N-furfurylidene-ethylamine instead of 30.95 g (0.243 mol) of N-butylidene-n-butylamine, and 36.9 g (0.684 mol) of 1,3-butadiene. The subsequent distillation gives 37.0 g (0.160 mol) of (1-furyl)-nonatrien (3,6,8)-yl-ethylamine; yield 72.7% of theory, relative to N-furfurylideneethylamine reacted (conversion 90.5%); boiling point 84–86° C/0.1 mm Hg; $n_D^{20}$ = 1.5122.

Analysis for $C_{15}H_{21}NO$: Calculated: C, 77.88%; H, 9.15%; N, 6.05%; O, 6.92%. Found: C, 77.9%; H, 9.4%; N, 5.75%; O, 6.7%.

Mass spectrum: molecule peak 231, fragment masses 230, 216, 164, 124 and 96;

$H^1$-NMR spectrum: τ [ppm]: 2.78(s), 3.3–4.6(m), 4.67(m), 5.04 and 5.15(m), 6.37(t), 7.30(m), 7.57(m), 8.49(s), 9.00(t) in the ratio 1:5:2:2:1:2:4:1:3;

IR spectrum (liquid): ν (>N—H) — 3300 $cm^{-1}$; ν (C=C—C=C) — 1650, 1600 $cm^{-1}$; δ (—CH=$CH_2$) — 1005, 900 $cm^{-1}$;

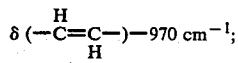

δ (—$CH_3$) — 1375 $cm^{-1}$.

EXAMPLE 43

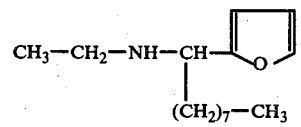

The [1-furyl-(2)]-nonatrien-(3,6,8)-yl-ethylamine, prepared in accordance with Example 42, is hydrogenated at normal pressure and room temperature (25° c), using a palladium-charcoal catalyst in methanol/glacial acetic acid (volume ratio 3:1), and with the absorption of 3 mols of hydrogen, to give [1-furyl-(2)]-nonyl-ethylamine; boiling point 141–142.5° C./9 mm Hg; $n_D^{20}$ = 1.4644.

Analysis for $C_{15}H_{27}NO$: Calculated: C, 75.90%; H, 11.46%; N, 5.90%. Found: C, 75.67%; H, 11.35%; N, 5.60%.

Mass spectrum: molecule peak 237; fragment masses 236, 208, 193, 170 and 124;

$H^1$-NMR spectrum τ [ppm]: 2.74(d), 3.79(dd), 3.96 (d), 6.40(t), 7.53(quartet) and 7.61(s), 8.30(m), 8.79(s), 8.97(t), 9.16(t) in the ratio 1:1:1:1:3:2:12:3:3.

EXAMPLE 44

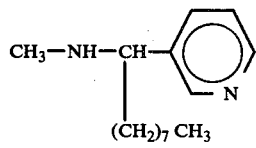

The (1-m-pyridyl)-nonatrien-(3,6,8)-yl-methylamine, prepared in accordance with Examples 35 and 36, is hydrogenated at normal pressure and room temperature (25° C), using a palladium-charcoal catalyst in glacial acetic acid/methanol (volume ratio 1:3), and with the absorption of 3 mols of hydrogen, to give (1-m-pyridyl)-nonyl-methylamine; boiling point 98–99° C./0.001 mm Hg; $n_D^{20}$ = 1.4972.

Analysis for $C_{15}H_{26}N_2$: Calculated: C, 76.9%; H, 11.1%; N, 12.9%. Found: C, 76.3%; H, 10.7%; N, 12.1%.

Mass spectrum: molecule peak 234, fragment masses 233, 204, 156, 121 and 94;

$H^1$-NMR spectrum: τ [ppm]: 1.59(d) and 1.62(d), 2.45(m), 2.87(m), 6.59(m), 7.62(s), 7.80(s), 8.39(m), 8.81(s), 9.18(t) in the ratio 2:1:1:1:1:3:2:12:3.

EXAMPLE 45

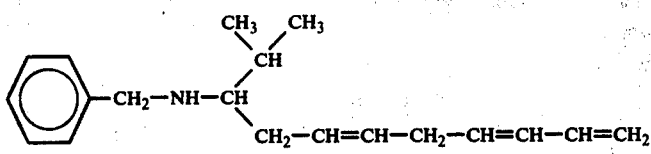

The procedure is as described in Example 22, but using 65.6 g (0.408 mol) of N-isobutylidene-benzylamine, 60 g (1.11 mols) of 1,3-butadiene and 14.6 g (0.168 mol) of morpholine. The reaction is complete after 20 hours. Distillation gives 57.1 g (0.212 mol) of (1-isopropyl)-nonatrien-(3,6,8)-yl-benzylamine; yield 95.9% of theory, relative to N-isobutylidene-benzylamine reacted (conversion 54.3%); boiling point 99–101° C./0.001 mm Hg; $n_D^{20} = 1.5274$.

Analysis for $C_{19}H_{27}N$: Calculated: C, 84.7%; H, 10.1%; N, 5.2%. Found: C, 83.79%; H, 10.13%; N, 5.29%.

Mass spectrum: molecule peak 269, fragment masses 268, 254, 226 and 162;

$H^1$-NMR spectrum: τ [ppm]: 2.82(s), 3.3–4.5(m), 4.65(m), 5.02(m) and 5.13(m), 6.35(s), 7.24(m), 7.74(quin), 8.00(m) and 8.24(m), 8.78(s), 9.14(d) in the ratio 5:3:2:2:2:2:1:3:1:6;

IR spectrum (liquid) ν (C≡C—C≡C) — 1650, 1600 $cm^{-1}$, δ (—CH=CH$_2$)— 900, 1005 $cm^{-1}$, $$\delta \; (-\overset{H}{\underset{H}{C}}{=}C-) - 970 \; cm^{-1},$$

$$\delta \; (-CH\overset{CH_3}{\underset{CH_3}{\diagup\diagdown}}) - 1365, 1380 \; cm^{-1}.$$

EXAMPLE 46

If morpholine is not used in Example 45, an otherwise identical procedure gives (1-isopropyl)-nonatrien-(3,6,8)-yl-benzylamine in a yield of 53.3% of theory, relative to N-isobutylidene-benzylamine reacted (conversion 41.5%).

EXAMPLE 47

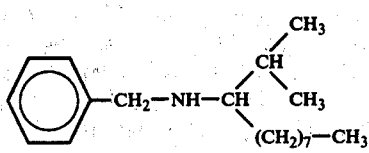

The (1-isopropyl)-nonatrien-(3,6,8)-yl-benzylamine, prepared in accordance with Examples 45 and 46, is hydrogenated at normal pressure and room temperature (25° C.), using a Raney-nickel catalyst in methanol, and with the absorption of 3 mols of hydrogen, to give (1-isopropyl)-nonyl-benzylamine; boiling point 96–99° C./0.001 mm Hg; $n_D^{23} = 1.4807$.

Analysis for $C_{19}H_{33}N$: Calculated: C, 82.9%; H, 12.0%; N, 5.1%. Found: C, 82.7%; H, 12.3%; N, 5.2%.

Mass spectrum: molecule peak 275, fragment masses 274, 260, 232 and 162;

$H^1$-NMR spectrum: τ [ppm]: 2.68(m), 6.23(s), 7.66(m), 8.23(m), 8.71(s), 8.89(s), 9.10(t) and 9.11(d) in the ratio 5:2:1:3:12:1:9.

EXAMPLE 48

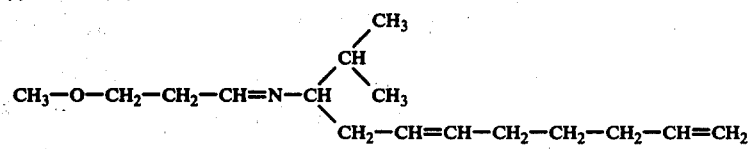

The procedure is as described in Example 1, but using 47.1 g (0.329 mol) of N-isobutylidene-(3-methoxy)-propylamine instead of 30.95 g (0.243 mol) of N-butylidene-n-butylamine, and 45.1 g (0.834 mol) of 1,3-butadiene. Distillation gives 42.7 g (0.171 mol) of N-(3-methoxy)-propylidene-(1-isopropyl)-nonadien-(3,8)-yl-amine; yield 57.4% of theory, relative to N-isobutylidene-(3-methoxy)-propylamine reacted (conversion 90.6%); boiling point 84–86° C./0.001 mm Hg; $n_D^{20} = 1.4609$.

Analysis for $C_{16}H_{29}NO$: Calculated: C, 76.46%; H, 11.62%; N, 5.57%. Found: C, 76.55%; H, 11.71%; N, 5.66%.

Mass spectrum: molecule peak: none; fragment masses 219, 204, 192, 176, 126 and 110;

$H^1$-NMR spectrum: τ [ppm]: 2.53(t), 4.38(m), 4.78(m), 5.11(m) and 5.15(m), 6.48(t), 6.75(s), 7.53(m), 7.81(m), 8.05(m), 8.28(m), 8.59(quin), 9.16 and 9.19(dd) in the ratio 1:1:2:2:2:3:3:2:4:1:2:6;

IR spectrum (liquid): ν (C=N) — 1670 $cm^{-1}$, ν(C=C) — 1640 $cm^{-1}$, δ (—CH=CH$_2$) — 909, 990 $cm^{-1}$, $$\delta \; (-\overset{H}{\underset{H}{C}}{=}C-) \cdot 965 \; cm^{-1}, \; \delta \; (-CH\overset{CH_3}{\underset{CH_3}{\diagup\diagdown}}) - 1365, 1380 \; cm^{-1}.$$

EXAMPLE 49

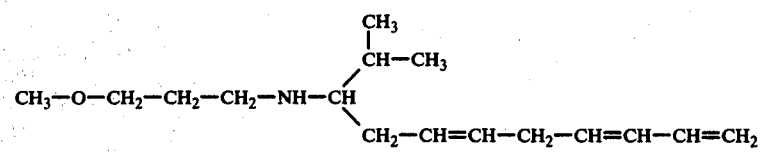

The procedure is as described in Example 22, but using 47.8 g (0.334 mol) of N-isobutylidene-(3-methoxy)-propylamine, 45.3 g (0.837 mol) of 1,3-butadiene and 29.8 g (0.342 mol) of morpholine. Distillation gives 38.6 g (0.154 mol) of (1-isopropyl)-nonatrien-(3,6,8)-yl-(3-methoxy)-propylamine; yield 46.7% of theory, relative to N-isobutylidene-(3-methoxy)-propylamine reacted (conversion 99%); boiling point 86–89° C./0.001 mm Hg; $n_D^{20}$ = 1.4905.

Analysis for $C_{16}H_{29}NO$: Calculated: C, 76.5%; H, 11.6%; N, 5.5%; O,6.4%.

Found: C, 75.7%; H, 11.4%; N, 5.4%; O,6.9%.

Mass spectrum: molecule peak 251, fragment masses 250, 236, 208 and 144;

H¹-NMR spectrum: τ [ppm]: 3.3–5.2(m), 6.49(t), 6.75(s), 7.0–7.5(m), 7.7–8.5(m), 8.85(s), 9.08(d) in the ratio 7:2:3:3:7:1:6;

IR spectrum (liquid) $\nu$ (C=C—C=C) — 1643, 1600 cm⁻¹, $\nu$ (\N—H) - 3320 cm⁻¹, δ (—CH=CH₂) - 900, 1000 cm⁻¹,

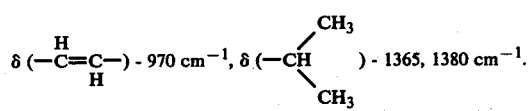

EXAMPLE 50

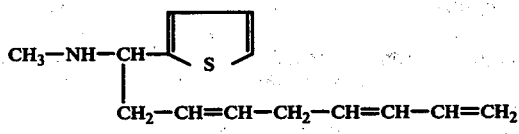

The procedure is as described in Example 22, but using 47.7 g (0.381 mol) of N-2-thenylidene-methylamine, 46.0 g (0.853 mol) of 1,3-butadiene and 29.0 g (0.334 mol) of morpholine. Distillation gives 55.3 g (0.238 mol) of [1-thienyl-(2)]-nonatrien-(3,6,8)-yl-methylamine; yield 62.8% of theory, relative to N-2-thenylidene-methylamine reacted (conversion 99.3%); boiling point 84–86° C./0.001 mm Hg; $n_D^{20}$ = 1.5506.

Analysis for $C_{14}H_{19}NS$: Calculated: C, 72.06%; H, 8.20%; N, 6.00%; S, 13.74%. Found: C, 71.43%; H, 8.34%; N, 6.25%; S, 13.30%.

Mass spectrum: molecule peak 233, fragment masses 126;

H¹-NMR spectrum: τ [ppm]: 2.91(m), 3.21(m), 3.2–4.5(m), 4.64(m), 5.01(m) and 5.13(m), 6.28(t), 7.25(m), 7.64(m), 7.73(s), 8.56(s) in the ratio 1:2:3:2:2:1:2:2:3:1;

IR spectrum (liquid):

$\nu$(\N—H) - 3320 cm⁻¹;

$\nu$ (C=C—C=C) — 1645, 1600 cm⁻¹, δ (—CH—CH₂) — 900, 1000 cm⁻¹,

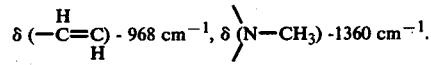

Example 51

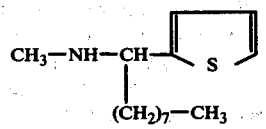

The [1-thienyl-(2)]nonatrien-(3,6,8)-yl-methylamine, prepared in accordance with Example 50, is hydrogenated at normal pressure and room temperature, using a palladium-charcoal catalyst in methanol/glacial acetic acid (volume ratio 3:1), and with the absorption of 3 mols of hydrogen, to give [1-thienyl-(2)]-nonyl-methylamine; boiling point 81–83° C/0.001 mm Hg; $n_D^{20}$ = 1.4976.

Analysis for $C_{14}H_{25}NS$: Calculated: C, 70.3%; H, 10.5%; N, 5.8%; S, 13.4%. Found: C, 70.7%; H, 10.8%; N, 5.8%; S, 13.3%.

Mass spectrum: molecule peak 239, fragment masses 210, 166, 156, 129 and 126;

H¹-NMR spectrum: τ [ppm]: 2.91 (dd), 3.18(m), 6.34(t), 7.74(s), 8.95(m), 8.66(s), 8.80(s), 9.18(t) in the ratio 1:2:1:3:2:1:12:3.

EXAMPLE 52

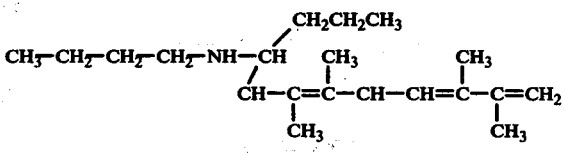

The procedure is as described in Example 22, but using 50.7 g (0.4 mol) of N-butylidene-n-butylamine, 75.9 g (0.925 mol) of 2,3-dimethyl-1,3-butadiene and 24.3 g (0.279 mol) of morpholine. The reaction time is 20 hours. Distillation gives 10.8 g (0.0372 mol) of [N-(1-propyl)-3,4,7,8-tetramethyl-nonatrien-(3,6,8)-yl]-butylamine; yield 18.4% of theory, relative to N-butylidene-n-butylamine reacted (conversion 50.6%); boiling point 97–104° C/0.001 mm Hg; $n_D^{20}$ = 1.4837.

Analysis for $C_{10}H_{37}N$: Calculated: C, 82.5%; H, 12.7%; N, 4.8%. Found: C, 81.1%; H, 12.7%; N, 4.9%.

H¹-NMR spectrum: τ [ppm]: 4.5–5.3(m), 7.42(m), 7.7(m), 8.09(m), 8.40(m), 8.65(m), 8.95(s), 9.11(t) in the ratio 3:2:2:3:12:8:1:6;

Mass spectrum: molecule peak 291, fragment masses 276, 248, 220, 194, 166 and 128;

IR spectrum: $\nu$ (>N—H) - 3300 cm⁻¹, $\nu$ (C=C—C=C) — 1640, 1600 cm⁻¹, δ (>C=CH₂) — 888 cm⁻¹, δ (—CH₃) — 1380 cm⁻¹.

EXAMPLE 53

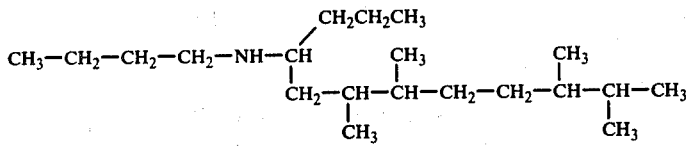

The [N-(1-propyl)-3,4,7,8-tetramethyl-nonatrien-(3,6,8)-yl]-butylamine, prepared in accordance with Example 52, is hydrogenated at normal pressure and room temperature (25° C), using a palladium-charcoal catalyst in glacial acetic acid/methanol (volume ratio 1:3), and with the absorption of 3 mols of hydrogen, to give [N-(1-propyl)-3,4,7,8-tetramethylnonyl]-butylamine; boiling point 105–108° C./0.001 mm Hg; $n_D^{20}$ = 1.4537.

Analysis for $C_{20}H_{43}N$: Calculated: C, 80.9%; H, 14.5%; N, 4.7%. Found: C, 80.6%; H, 14.7%; N, 4.5%.

Mass spectrum: molecule peak 297, fragment masses 282, 254, 224, 128 and 86;

$H^1$-NMR spectrum: τ [ppm]: 7.45(m), 8.3–8.9(m), 9.0–9.25(m) in the ratio 3:18:22.

$H^1$-NMR spectrum: τ [ppm]: 2.51(t), 4.29(m), 4.71(m), 5.11(m) and 5.15(m), 7.98(m), 8.74(s), 8.92(s), 9.15(t) in the ratio 1:1:2:2:8:12:6:3;

IR spectrum (liquid): ν (C=N) — 1670 cm$^{-1}$, ν (C=C) — 1645 cm$^{-1}$, δ (—CH=CH$_2$) — 908, 990 cm$^{-1}$,

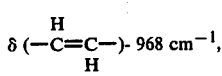

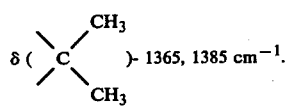

EXAMPLE 54

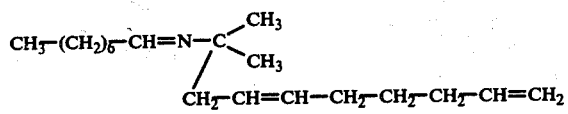

4.4 g (17.0 mmols) of nickel acetylacetonate and 4.5 g (17.2 mmols) of triphenylphosphine, in 164 g of absolute toluene in which 15.0 g (0.278 mol) of 1,3-butadiene are dissolved, are reduced at 0° to 20° C. by means of 5.6 g (43 mmols) of ethoxydiethyl-aluminium. After stirring the reaction mixture for one hour at 20° C., a clear, orange-red catalyst solution is formed. The catalyst solution is then heated to 85° C while 1,3-butadiene is continuously introduced, and 90.2 g (0.534 mol) of N-isopropylidene-n-octylamine are added dropwise over the course of 30 minutes. In the course thereof the heating bath is removed and the rate of dropwise addition is regulated in such a way that the reaction temperature is 85–90° C. The reaction solution is then cooled to 0° C., 23 g (74.1 mmols) of triphenyl phosphite are added in order to deactivate the catalyst and the mixture is distilled. A 1st fraction which contains 163 g of toluene and 18.1 g (0.107 mol) of unreacted N-isopropylidene-n-octylamine (gas chromatogram) is obtained here at a bath temperature of up to 50° C. and a vacuum of 0.2 mm Hg. A subsequent refining distillation gives 84.0 g(0.304 mol) of N-octylidene-(1,1)-dimethyl)-nonadien-(3,8)-yl-amine; yield 71.1% of theory, relative to N-isopropylidene-n-octylamine reacted (conversion 80.0%); boiling point 86–93° C./0.01 mm Hg; $n_D^{20}$ = 1.4506.

Analysis for $C_{19}H_{35}N$: Calculated: C, 82.3%; H, 12.65%; N, 5.05%. Found: C, 81.8%; H, 12.4%; N, 5.0%.

Mass spectrum: molecule peak 277, fragment masses 276, 262 and 168;

EXAMPLE 55

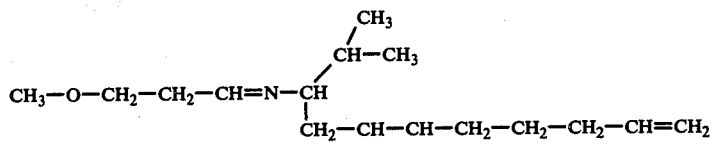

The procedure is as described in Example 54, but using 240.0 g (1.68 mols) of N-isobutylidene-(3-methoxy)propylamine instead of 90.2 g (0.534 mol) of N-isopropylidene-n-octylamine. Distillation gives 214.1 g (0.855 mol) of [N-(3-methoxy)-propylidene]-(1-isopropyl)-nonadien-(3,8)-yl-amine; yield 67.7% of theory, relative to N-isobutylidene-[(3-methoxy)-propylamine] reacted (conversion 77.6%); boiling point 84 – 86° C./0.001 mm Hg; $n_D^{20}$ = 1.4606.

Analysis for $C_{16}H_{29}NO$: calculated: C, 76.50%; H, 11.55%; N, 5.60%; O, 6.36%. Found: C, 76.52%; H, 11.80%; N, 5.49%; O, 6.25%.

Mass spectrum; molecule peak: none; fragment masses 252, 236, 208, 176, 150, 142, 110 and 84;

$H^1$-NMR spectrum τ [ppm]: 2.50(t), 4.25(m), 4.73(m), 5.08(m) and 5.11(m), 6.46(t), 6.71(s), 7.48(m), 7.75(m), 8.03(quin), 8.26(m), 8.58(quin), 9.16(d) and 9.20(d) in the ratio 1:1:2:2:2:3:3:2:4:1:2:6;

IR spectrum (liquid): ν (>N—H) — 3300 cm$^{-1}$, ν(C=N) — 1672 cm$^{-1}$, ν(C=C) — 1645 cm$^{-1}$, δ (—CH=CH$_2$) — 910, 990 cm$^{-1}$,

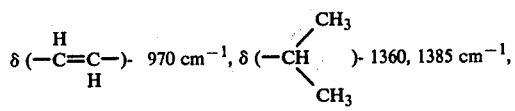

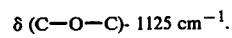

EXAMPLE 56

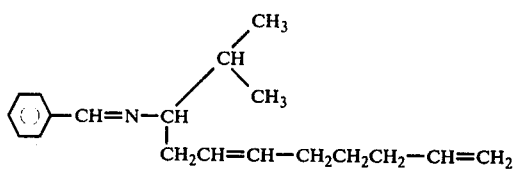

The procedure is as described in Example 54, but using 431.0 g (2.68 mols) of N-isobutylidene-benzylamine instead of 90.2 g (0.534 mol) of N-isopropylidene-n-octylamine. Distillation gives 344.8 g (1.285 mols) of N-benzylidene-(1-isopropyl)-nonadien-(3,8)-yl-amine; yield 73.0% of theory, relative to N-isobutylidene-benzylamine reacted (conversion 65.7%); boiling point 104 106° C./0.001 mm Hg; $n_D^{20} = 1.5194$.

Analysis for $C_{19}H_{27}N$: Calculated: C, 84.8%; H, 10.0%; N, 5.2%. Found: C, 84.32%; H, 10.01%; N, 5.15%.

Mass spectrum: molecule peak 269, fragment masses 268, 254, 226, 160, 143 and 91;

H¹-NMR spectrum: τ [ppm]: 1.93(s), 2.33(m), 2.71(m), 4.19(m), 4.70(m), 5.15(m) and 5.18(m), 7.20(qu), 7.69(m), 8.10(m), 8.65(m), 9.12(d) in the ratio 1:2:3:1:2:2:1:2:5:2:6;

IR spectrum (liquid): $\nu(C=N)$ — 1650 cm⁻¹, $\nu(C=C)$ — 1642 cm⁻¹, δ (—CH=CH₂)— 910, 990 cm⁻¹,

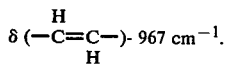

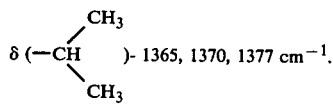

EXAMPLE 57

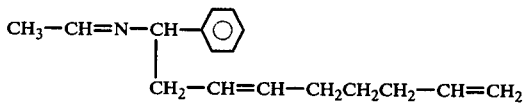

The procedure is as described in Example 54, but using 360 g (2.71 mols) of N-benzylidene-ethylamine instead of 90.2 g (0.534 mol) of N-isopropylidene-n-octylamine. Distillation gives 115.7 g (0.48 mol) of N-ethylidene-(1-phenyl)-nonadien-(3,8)-yl-amine; yield 49.5% of theory, relative to N-benzylidene-ethylamine reacted (conversion 35.8%), boiling point 87–89° C./0.01 mm Hg; $n_D^{20} = 1.5185$.

Analysis for $C_{17}H_{23}N$: Calculated: C, 84.65%; H, 9.55%; N, 5.8%. Found: C, 84.12%; H, 9.62%; N, 5.94%.

Mass spectrum: molecule peak: none; fragment masses 194, 134, 106 and 79;

H¹-NMR spectrum: τ [ppm]: 2.32(qu), 2.72(m), 4.23(m), 4.65(m), 5.05(m) and 5.08(m), 5.98(t), 7.49(m), 8.64(quin) in the ratio 1:5:1:2:2:1:2:7:2;

IR spectrum (liquid): $\nu(C=N)$ — 1670 cm⁻¹, $\nu(C=C)$ — 1645 cm⁻¹, δ (—CH=CH₂) — 908, 990 cm⁻¹,

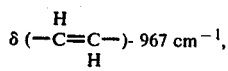

δ (—CH₃) — 1355, 1375, cm⁻¹.

The new compounds of the formula Ia and Ib, and particularly the saturated compounds of the formula Ic, exhibit an anti-microbial action and are, therefore, suitable for combating harmful micro-organisms, for example in material protection.

The anti-microbial compounds of the present invention can be used on a very broad basis, particularly to protect organic substrates against attack by harmful and pathogenic micro-organisms. The anti-microbial agents mentioned are, therefore, suitable as preservatives and disinfectants for industrial products of all kinds.

Amongst the industrial products which can be preserved or disinfected with the aid of the compounds, according to the invention, of the formulae Ia - Ic, the following may be mentioned as examples: glues, binders, paints, for example paints for walls and ceilings, containing an albuminous paint binder, textile auxiliaries, textile finishing agents, permanent sizes based on polyvinyl alcohol, animal mucilages and oils, lacquers and paints, dyeing or printing pastes and similar preparations based on organic and inorganic dyestuffs or pigments, and also those which contain casein or other organic compounds as an admixture, printing thickeners made from starch or cellulose derivatives, plasticisers, substances which tend to rot, such as leather and wood, celluloses, viscose spinning compositions and paper.

The compounds according to the invention can be employed in the cellulose and paper industry, for example for preventing the known formation of slime, which is caused by micro-organisms, in the equipment used for making paper.

The action of the compounds according to the invention can also be utilised in preservative and disinfectant finishes for plastics, for example polyamides and polyvinyl chloride. When using plasticisers it is advantageous to add the antimicrobial additive, dissolved or dispersed in the plasticiser, to the plastic. Plastics with antimicrobial properties can be used for all kinds of use articles in which an activity against the most diverse germs, such as, for example, bacteria and fungi, is desired, that is to say, for example, for foot mats, bathroom curtains, toilet seats, foot grids in swimming pools, wall coverings and the like. Floor and furniture maintenance materials with a disinfectant action are obtained by incorporating the compounds into suitable compositions of wax and polish.

The use forms of the active substances according to the invention can correspond to the usual formulations. Thus, the active substances can be used, for example, in the form of solutions, dispersions or emulsions, aerosols (sprays) and the like. Since the active compounds of the formula Ia - Ic are, for the most part, insoluble in water or are only sparingly soluble in water, customary organic solvents, such as toluene, xylene, methylcellosolve, acetone or tetrahydrofurane, to which dispersing agents, for example emulsifiers, such as sulphonated castor oil, fatty alcohol sulphates and the like, and/or other auxiliary materials can additionally be added, are used for the preparation of solutions. Depending on the application, customary wetting agents and dispersing agents can be added to dispersions of active compounds.

The content of active compounds in the agents according to the invention is generally between about 0.01 and 5 per cent by weight, preferably 0.1 to 3 per cent by weight, relative to the weight of the agent.

The compounds according to the invention can be used with advantage as preservative and disinfectant finishes for fibres and textiles, it being possible to apply them to natural and artificial fibres, where they display a permanent action against harmful micro-organisms, for example fungi and bacteria. The addition of the compounds can here take place before, simultaneously with or after a treatment of these textiles with other substances, for example dyeing or printing pastes, flameproofing agents, agents for imparting a soft handle, other finishes and the like.

Textiles treated in this way also exhibit a protection against the occurrence of perspiration odour, such as is caused by micro-organisms.

The agents used for the finishing or protection of textiles should contain the active substances according to the invention in a finely divided form. Particular use is therefore made of solutions, dispersions and emulsions of the active substances. Aqueous dispersions can, for example, be obtained from pastes or concentrates and can be used in liquid form or as an aerosol.

The aqueous solutions or dispersions appropriately contain surface-active agents, for example anionic compounds, such as soaps and other carboxylates (for example alkali metal salts of high fatty acids), derivatives of sulphur-oxygen acids (for example the sodium salt of dodecylbenzenesulphonic acid, water-soluble salts of sulphuric acid monoesters of higher-molecular alcohols or of polyethylene glycol ethers of the latter, such as, say, soluble salts of dodecyl alcohol sulphate or of dodecyl alcohol polyethylene glycol ether sulphate), derivatives of phosphorus-oxygen acids (for example phosphates), derivatives with acid (electrophilic) nitrogen in the hydrophilic group (for example disulphinic salts), cationic surface-active agents, such as amines and their salts (for example lauryldiethylenetriamine), onium compounds or amine oxides, or non-ionic surface-active agents, such as polyhydroxy compounds, surface-active agents based on mono- or poly-saccharides, higher-molecular ethylene glycols or polyethylene glycol ethers (for example polyethylene glycol ethers of higher fatty alcohols or polyethylene glycol ethers of higher-molecular, alkylated phenols). In addition the liquor can also contain customary auxiliary materials, such as water-soluble perborates, polyphosphates, carbonates, silicates, optical brighteners, plasticisers, salts with an acid reaction, such as ammonium or zinc silicofluoride, or certain organic acids, such as oxalic acid, and also finishing agents, for example those based on synthetic resins or starch.

The textile materials can be impregnated with the active substances, for example by hot or cold, aqueous dye-baths, bleaching baths, chrome baths or after-treatment baths, it being possible to use various textile finishing processes, such as, for example, the padding process for the exhaustion process.

Owing to their greater solubility in organic solvents, the active substances are also well suited for application from non-aqueous media.

The active substances according to the present invention can be used on their own or together with other known antimicrobial agents for protecting textiles.

Possible textiles which are finished or protected are both fibres of natural origin, such as those containing cellulose, for example cotton, or those containing polypeptides, for example wool or silk, or fibre materials of synthetic origin, such as those based on polyamide, polyacrylonitrile or polyester, or mixtures of these fibres.

In most cases the textile materials are adequately protected against attack by fungi and bacteria by means of a content of 0.01 to 5% by weight, preferably 0.1 to 3% by weight, of the active substance, relative to the weight of the textile materials.

By combining the compounds according to the invention with surface-active substance, particularly detergent substance, washing and cleansing agents with an excellent antibacterial or anti-mycotic action are obtained. The washing and cleansing agents can be present in any desired form, for example in liquid, pasty, solid, flake or granular form. In order to prepare such agents, the compounds according to the invention can be incorporated into anionic, cationic or non-ionic surface-active agents of the kind mentioned previously or into mixtures of surface-active agents of various kinds.

Aqueous preparations of such washing and cleansing agents, containing compounds according to the invention, can be used, for example, for the antimicrobial finishing of textile materials. They are also suitable as antimicrobial cleansing agents in the food and drink industry, for example in breweries, dairies, cheese factories and slaughterhouses.

For disinfectant and preservative purposes, the compounds of the formulae Ia to Ic can also be used in combination with known antimicrobial agents. These include, for example:

Halogens and halogen compounds containing active halogen, for example sodium hypochlorite, calcium hypochlorite, chloride of lime, sodium p-toluenesulphochloroamide, p-toluenesulphodichloroamide, N-chlorosuccinimide, 1,3-dichloro-5,5-dimethylhydantoin, trichloroisocyanuric acid, potassium dichloroisocyanurate, iodine, iodine trichloride and complex compounds of iodine and iodine trichloride with surface-active agents such as polyvinyl pyrrolidone, alkylphenoxy-polyglycols, polyoxypropylene glycols, alkylaminoethanesulphonic acids and alkylaminoethanesulphonates, alkylarylsulphonates and quaternary ammonium compounds.

Boron compounds, for example boric acid and borax.

Organometallic compounds, for example bis-tribuyl-tin oxide, triphenyl-tin hydroxide, tributyl-tin salicylate, tributyltin chloride, phenyl-mercury borate and phenyl-mercury acetate.

Alcohols, for example hexyl alcohol, trichloroisobutyl alcohol, 1,2-propylene glycol, triethylene glycol, benzyl alcohol, 4-chlorobenzyl alcohol, 2,4- and 3,4-dichlorobenzyl alcohol, 2-phenylethyl alcohol, 2-(4-chlorophenyl)-ethyl alcohol, ethylene glycol monophenyl ether, methanol linalool and 2-bromo-2-nitro-1,3-propanediol.

Aldehydes, for example formaldehyde, paraformaldehyde, gutaraldehyde, benzaldehyde, 4-chlorobenzaldehyde, 2,4- and 3,4-dichlorobenzaldehyde, cinnamaldehyde, salicylaldehyde, 3,5-dibromosalicylaldehyde, 4-hydroxybenzaldehyde, anisaldehyde and vanillin.

Carboxylic acids and derivatives, for example trichloroacetic acid, monobromoacetic acid glycol ester, Na and Ca propionate, caprylic acid, undecylenic acid, Zn undecylenate, sorbic acid, K and Ca sorbate, lactic acid, malonic acid, aconitic acid, citric acid, benzoic acid, 4-chlorobenzoic acid, benzoic acid benzyl ester, salicylic acid, 4-chlorosalicyclic acid n-butylamide, salicylanilide, 3,4',5-tribromosalicylanilide, 3,3',4',5-tetrachlorosalicylanilide, 4-hydroxybenzoic acid, 4-hydroxybenzoic acid ethyl ester, gallic acid, mandelic acid, phenylpropionic acid, phenoxyacetic acid, dehydracetic acid and vanillic acid propyl ester.

Phenols, for example phenol, mono- and poly-chlorophenols, cresols, 4-chloro-3-methylphenol, 4-chloro-3,5-dimethylphenol, thymol, 4-chlorothymol, 4-t-amylphenol, saligenin, 4-n-hexylresorcinol, carvacrol, 2-phenylphenol, 2-benzyl-4-chlorophenol, 2,2'-dihydroxy-5,5'-dichlorodiphenylmethane, 2,2'-dihydroxy-3,3',5,5',6,6'-hexachlorodiphenylmethane, 2,2'-dihydroxy-5,5'-dichlorodiphenyl sulphide, 2,2'-dihydroxy-3,3',5,5=-tetrachlorodiphenyl sulphide, 2-hydroxy-2',4,4'-trichlorodiphenyl ether and dibromosalicyl.

Quinones, for example 2,5-dimethylquinone, 2,3,5,6-tetrachlorobenzoquinone and 1,4- or 2,3-dichloro-1,4-naphthoquinone.

Carbonic acid derivatives, for example pyrocarbonic acid diethyl ester, tetramethylthiuram sulphide, 3,4,4'-trichloro-N,N'-diphenylurea, 3-trifluoromethyl-4,4'-dichloro-N,N'-diphenylurea, N-3-trifluoromethylphenyl-N'-2-ethylhexylurea, 1,6-bis-(4'-chlorophenyl-diguanidino)-hexane, dodecylmethylguanidine acetate, ammonium thiocyanate and 4,4'-diamidino-α,ω-diphenoxyhexane.

Amines, for example dodecylpropylenediamine, dodecyldiethylenetriamine and diaminobenzene dihydroiodide.

Quaternary ammonium compounds, for example alkyl-dimethylbenzylammonium chloride, alkyl-dimethyl-ethylbenzylammonium chloride, dodecyl-dimethyl-3,4-dichlorobenzylammonium chloride, dodecyl-di-(2-hydroxyethyl)-benzylammonium chloride, dodecyldi-(2-hydroxyethyl)-benzylammonium pentachlorophenolate, dodecyl-di-(2-hydroxyethyl)-benzylammonium 4-methylbenzoate, dodecyl-dimethylphenoxyethylammonium bromide, 4-diisobutyl-phenoxyethoxyethyl-dimethylbenzylammonium chloride, 4-diisobutyl-cresoxyethoxyethyl-dimethylbenzylammonium chloride, dimethyl-didecylammonium chloride, cetyl-trimethylammonium bromide, dodecyl-pyridinium chloride, cetyl-pyridinium chloride, dodecyl-isoquinolinium chloride, decamethylene-bis-4-aminoquinaldinium dichloride, α-(p-tolyl)-dodecyl-trimethylammonium methosulphate and (dodecanoyl-N-methylaminoethyl)(phenylcarbamoylmethyl)-dimethylammonium chloride.

Quaternary phosphonium compounds, for example dodecyltriphenylphosphonium bromide.

Amphoteric compounds, for example dodecyl-di-(aminoethyl)glycine.

Heterocyclic compounds, for example 2-mercaptopyridine-N-oxide, the Na and Zn salt of 2-mercaptopyridine-N-oxide, 2,2'-dithiopyridine-1,1'-di-N-oxide, 8-hydroxyquinoline, 5-chloro-8-hydroxyquinoline, 5-chloro-7-iodo-8-hydroxyquinoline, 5,7-dichloro-8-hydroxyquinoline, 5,7-dichloro-8-hydroxyquinaldine, bis-2-methyl-4-aminoquinolylcarbamide hydrochloride, 2-mercaptobenzthiazole, 2-(2'-hydroxy-3',5'-dichlorophenyl)-5-chlorobenzimidazole, 2-aminoacridine hydrochloride, 5,6-dichlorobenzoxazolone, 1-dodecyl-2-iminoimidazoline hydrochloride and 6-chlorobenzisothiazolone.

Determination of the minimum inhibitory concentrations (MTC) against bacteria and fungi 1.5% strength stock solutions, in methylcellosolve, of the compounds according to the invention, for example (1-phenyl)-nonylmethylamine, (1-phenyl)-nonylethylamine, (1-phenyl)-nonyl-n-propylamine, (1,1-dimethyl)-nonatrien-(3,6,8)-yl-n-octylamine, (1,1-dimethyl)-nonyl-n-octylamine, [1-(4-chlorophenyl)]-nonatrien-(3,6,8)-yl-methylamine, [1-furyl-(2)]-nonylethylamine, (1-isopropul-nonylbenzylamine, [1-thienyl-(2)]-nonylmethylamine and (1-n-propyl)-nonylcyclohexylamine, are prepared and these are subsequently diluted in such a way that the incorporation in each case of 0.3 ml of the stock solutions and of more dilute solutions made from them in 15 ml of warm nutrient agar gives a series of concentrations of 300, 100, 30, 10, 3, 1 and so on ppm of active substance in the agar. The mixtures are case whilst still warm into plates and, after solidification, are inoculated with the following test organisms:

Gram-positive bacteria

*Staphylococcus aureus*
*Streptococcus faecalis*
*Streptococcus agalactiae*
*Streptococcus agalactiae*
*Bacillus subtilis*

Gram-negative bacteria

*Escherichia coli*
*Salmonella pullorum*
*Salmonella cholerae-suis*
*Proteus vulgaris*

Fungi

*Trichophyton mentagrophytes*
*Candida albicans*
*Aspergillus elegans*

After an incubation period of 48 hours at 37° C. (bacteria) or 5 days at 28° C. (fungi), a determination is made of the minimum limiting concentration (ppm) of the active substance at which the growth of the test organisms is stopped.

For the above compounds values of MIC are determined which are distinctly below the initial concentration of 300 ppm, for the fungi and/or bacteria mentioned.

Determination of the Microbiocidal Action

A. In order to establish whether the active substances have destroyed the test germs employed in the previous experiment (biocidal effect) or merely inhibited their growth (biostatic effect), circles of sterile filter paper with a diameter of 20 mm are placed on the inoculation areas of the germs which show no growth and, after a contact time of 30 minutes, the germs are transferred by means of these circles to sterile agar which has been blocked in respect of the active substances by means of Tween 80. The contact time is once more 30 minutes. If no growth of the transferred germs is observed on the secondary plate, the germs on the first have been destroyed by the active substance, that is to say, in the concentration concerned, the active substance exerts a biocidal effect on the germs tested.

The following additional test is carried out in order to confirm the determination given above:

B. Solutions of the following composition are prepared using the active substances mentioned: 5% of active substance, 5% of Na N-coconut-β-aminopropionate, 20% of Permutit-treated water and 70% of ethylcellosolve (ethylene glycol monoethyl ether).

Aliquot parts of these solutions are converted by means of sterile, distilled water into emulsions having an active substance content of 1,000 ppm, 500 ppm, 250 ppm and 125 ppm.

9.9 ml samples of the emulsions are inoculated with 0.1 ml of germ suspensions (approx. $10^7$ germs/ml).

Test Organisms

*Straphylococcus aureus*
*Streptococcus faecalis*
*Bacillus subtilis*
*Proteus vulgaris*

After a one minute duration of action, a loop of each of the inoculated emulsions is put into 10 ml of sterile brain-heart infusion broth, and the latter is then incubated for 24 hours at 37° C. and then assessed for turbidity (growth of germs). The loop is a measure which is made of platinum wire and has a defined diameter, and is standardised for microbiological purposes.

In the above experiments the compounds tested showed a biocidal action.

Treatment of Textiles

The compounds according to Examples 23, 27, 28, 28a, 31, 41, 43, 47 and 51 are dissolved in a suitable formulation (ethylcellosolve/dimethylformamide). The three substrates listed below are put into the formulation baths and are then squeezed out between two aluminium foils; the substrates are then dried in air. They are squeezed out in such a way that 2,500 ppm of active substance are located on the fabric in case (a), 250 ppm in case (b) and 25 ppm in case (c).

Substrates:

1. Cotton, renforcé, mercerised, bleached, weight 121 g/m².
2. Polyamide, nylon staple fabric, set, bleached, weight 140 g/m².
3. Polyester, Dacron staple fabric, type 54 set, bleached, weight 130 g/m².

The substrates are then tested against the test organisms mentioned below by the agar diffusion test (modified AATCC Test Method 90, 1970).

Bacteria

*Staphylococcus aureus* ATCC 6538
*Escherichia coli* NCTC 8196
*Proteus vulgaris* ATCC 9484

Fungi

*Candida albicans* ATCC 10259
*Trichophyton mentagrophytes* ATCC 9553
*Aspergillus elegans* M 3637.

The test plates consist of a two-layer agar, that is to say of a base layer of uninoculated nutrient agar and a covering layer of inoculated nutrient agar.
Bacteria: nutrient agar.
Fungi: mycophilic agar.

The filtered suspension of germs is poured onto a solidified base layer. After the inoculated layer has solidified, 20 mm diameter circles of the treated substrates are laid upon it. The bacteria and Candida plates are incubated for 24 hours at 37° C.; the fungi plates are incubated for 3 to 4 days at 28° C. After the incubation, the plates are evaluated in respect of the zone of inhibition. If there is no zone of inhibition, the growth under the test piece is checked using a magnifying glass.

The compounds tested in this way exhibit, in combination with the substrates used, a good action against the fungi and/or bacteria mentioned.

What we claim is:

1. A compound of the formula Ia

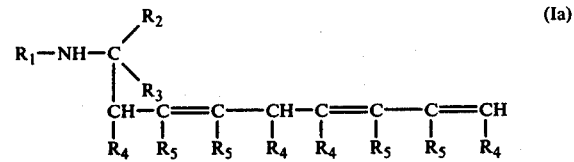

wherein $R_1$ is γ-methoxypropyl, an unsubstituted alkyl group having 1–18 carbon atoms, an unsubstituted cycloalkyl group having 5–8 carbon atoms, a benzyl or β-phenylethyl group, $R_2$ is hydrogen or an unsubstituted alkyl group having 1–18 carbon atoms and $R_3$ is hydrogen, an unsubstituted alkyl group having 1–18 carbon atoms, a benzyl or β-phenylethyl group, a phenyl group which is unsubstituted or is substituted by halogen atoms or alkyl or alkoxy groups having 1–4 carbon atoms, a naphthyl-1 or naphthyl-2group, or $R_2$ and $R_3$ conjointly form an unsubstituted 4-membered to 11-membered alkylene chain, provided that at least one of $R_1$ and $R_3$ contains one of the aryl moieties described above, the $R_4$ groups are each hydrogen and the $R_5$ groups are independently of one another hydrogen or methyl or the $R_4$ groups are each methyl and the $R_5$ groups are each hydrogen.

2. A compound of claim 1, wherein $R_1$ is an unsubstituted alkyl group having 1–8 carbon atoms, a cyclohexyl group or a benzyl group, $R_2$ is hydrogen or an unsubstituted alkyl group having 1–8 carbon atoms, $R_3$ is hydrogen, an unsubstituted alkyl group havine 1–8 carbon atoms, phenyl or chlorophenyl, and the $R_4$ and $R_5$ groups are each hydrogen.

3. A compound of claim 1, wherein $R_1$ is an unsubstituted alkyl group having 1–4 carbon atoms, $R_2$ is hydrogen or the methyl group, $R_3$ is the phenyl group, and the $R_4$ and $R_5$ groups are each hydrogen.

4. A compound as claimed in claim 1 having the formula

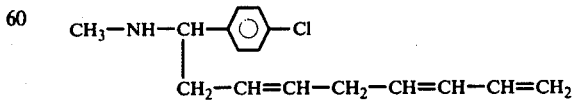

* * * * *